US009092559B2

(12) United States Patent
Niklewski et al.

(10) Patent No.: US 9,092,559 B2
(45) Date of Patent: Jul. 28, 2015

(54) DRUG DELIVERY SYSTEM WITH OPEN ARCHITECTURAL FRAMEWORK

(75) Inventors: Paul J. Niklewski, Cincinnati, OH (US); James F. Martin, Lebanon, OH (US); David Q. Feng, Mason, OH (US); Todd J. Mack, Loveland, OH (US); Donn C. Mueller, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 843 days.

(21) Appl. No.: 13/210,507

(22) Filed: Aug. 16, 2011

(65) Prior Publication Data
US 2013/0042863 A1 Feb. 21, 2013

(51) Int. Cl.
*G06F 19/00* (2011.01)

(52) U.S. Cl.
CPC .................... *G06F 19/3462* (2013.01)

(58) Field of Classification Search
CPC ............ A61M 5/172; A61M 16/0057; A61M 16/0063; A61M 16/00; A61B 5/0444; A61B 5/4362; A61B 5/0022; A61B 5/02; G06F 19/3418; G06F 19/3468; G06F 19/3462; G06F 19/3406; G06F 19/3456; G06F 3/0488; G01N 33/48792; G06Q 50/22; G06Q 50/24; G06Q 10/10; H04N 7/18
USPC .................. 604/19, 27, 48, 500, 503, 65–67; 128/200.24, 203.12, 203.15, 204.18, 128/204.21, 205.24
See application file for complete search history.

(56) References Cited

U.S. PATENT DOCUMENTS

| 5,630,799 | A | 5/1997 | Beiser et al. |
| 5,640,953 | A | 6/1997 | Bishop et al. |
| 5,685,314 | A | 11/1997 | Geheb et al. |

(Continued)

FOREIGN PATENT DOCUMENTS

| EP | 0735498 | 10/1996 |
| EP | 0735499 | 10/1996 |

(Continued)

OTHER PUBLICATIONS

Partial European Search Report dated Dec. 5, 2013 for Application No. EP 12180546.

(Continued)

*Primary Examiner* — Annette Dixon
(74) *Attorney, Agent, or Firm* — Frost Brown Todd LLC

(57) ABSTRACT

A medical system includes a sedation system and a central station in communication with the sedation system. The sedation system includes a monitoring unit and a drug delivery unit. The monitoring unit is operable to monitor at least one physiological parameter of a patient. The drug delivery unit is operable to deliver drugs to the patient based on data from the monitoring unit. The central station is operable to store patient related data and access a plurality of sedation systems. The central station may remotely control drug delivery through sedation systems, remotely provide voice instructions through sedation systems, display video feeds from sedation systems, respond to queries from sedation systems, and/or provide other functionalities. The system may also include an instrument that is operable to perform surgical and/or therapeutic procedures on the patient. The sedation system may provide power to the instrument and/or otherwise communicate with the instrument.

19 Claims, 15 Drawing Sheets

(56) References Cited

U.S. PATENT DOCUMENTS

| | | | |
|---|---|---|---|
| 5,752,917 A | 5/1998 | Fuchs | |
| 5,771,890 A | 6/1998 | Tamada | |
| 6,158,430 A * | 12/2000 | Pfeiffer et al. | 128/202.27 |
| 6,186,977 B1 | 2/2001 | Andrews et al. | |
| 6,349,724 B1 * | 2/2002 | Burton et al. | 128/204.18 |
| 6,406,426 B1 | 6/2002 | Reuss et al. | |
| 6,524,240 B1 | 2/2003 | Thede | |
| 6,593,528 B2 | 7/2003 | Franklin-Lees et al. | |
| 6,599,281 B1 | 7/2003 | Struys et al. | |
| 6,723,055 B2 | 4/2004 | Hoffman | |
| 6,745,764 B2 | 6/2004 | Hickle | |
| 6,807,965 B1 | 10/2004 | Hickle | |
| 6,938,619 B1 | 9/2005 | Hickle | |
| 6,982,564 B2 | 1/2006 | Akram et al. | |
| 6,986,347 B2 | 1/2006 | Hickle | |
| 7,034,692 B2 | 4/2006 | Hickle | |
| 7,150,735 B2 | 12/2006 | Hickle | |
| 7,152,604 B2 | 12/2006 | Hickle et al. | |
| 7,198,605 B2 | 4/2007 | Donofrio et al. | |
| 7,201,734 B2 | 4/2007 | Hickle | |
| 7,229,430 B2 | 6/2007 | Hickle et al. | |
| D546,947 S | 7/2007 | Nalagatla et al. | |
| 7,247,154 B2 | 7/2007 | Hickle | |
| 7,261,106 B2 | 8/2007 | Donofrio | |
| 7,299,981 B2 | 11/2007 | Hickle et al. | |
| 7,308,894 B2 | 12/2007 | Hickle | |
| D559,383 S | 1/2008 | Nalagatla et al. | |
| 7,316,231 B2 | 1/2008 | Hickle | |
| 7,338,470 B2 | 3/2008 | Katz et al. | |
| 7,367,339 B2 | 5/2008 | Hickle | |
| 7,527,052 B2 | 5/2009 | Hickle et al. | |
| 7,530,949 B2 | 5/2009 | Al Ali et al. | |
| 7,539,537 B2 | 5/2009 | Hickle | |
| 7,559,483 B2 | 7/2009 | Hickle et al. | |
| 7,565,905 B2 | 7/2009 | Hickle | |
| 7,578,802 B2 | 8/2009 | Hickle | |
| D613,184 S | 4/2010 | Nalagatla et al. | |
| 7,727,194 B2 | 6/2010 | Nalagatla et al. | |
| D621,722 S | 8/2010 | Nalagatla et al. | |
| 7,833,213 B2 | 11/2010 | Katz et al. | |
| 7,837,651 B2 | 11/2010 | Bishop et al. | |
| 7,935,081 B2 | 5/2011 | Flaker et al. | |
| 7,970,631 B2 | 6/2011 | Bruggeman et al. | |
| 7,992,556 B2 | 8/2011 | Hickle | |
| 7,997,271 B2 | 8/2011 | Hickle et al. | |
| 8,028,694 B2 | 10/2011 | Hickle | |
| 8,028,704 B2 | 10/2011 | Reynolds, II et al. | |
| 8,146,591 B2 | 4/2012 | Niklewski et al. | |
| 8,182,444 B2 | 5/2012 | Uber, III et al. | |
| 8,303,534 B2 | 11/2012 | Hickle et al. | |
| 8,555,876 B2 | 10/2013 | Hickle et al. | |
| 8,556,846 B2 | 10/2013 | O'Mahony et al. | |
| 8,567,393 B2 | 10/2013 | Hickle et al. | |
| 8,622,989 B2 | 1/2014 | Martin | |
| 2003/0074223 A1 | 4/2003 | Hickle et al. | |
| 2004/0073177 A1 | 4/2004 | Hickle | |
| 2004/0133187 A1 | 7/2004 | Hickle | |
| 2005/0070823 A1 | 3/2005 | Donofrio et al. | |
| 2006/0009733 A1 | 1/2006 | Martin | |
| 2006/0009734 A1 | 1/2006 | Martin | |
| 2006/0149321 A1 | 7/2006 | Merry et al. | |
| 2006/0206011 A1 * | 9/2006 | Higgins et al. | 600/300 |
| 2007/0191789 A1 | 8/2007 | Hickle | |
| 2007/0191817 A1 | 8/2007 | Martin | |
| 2007/0197881 A1 * | 8/2007 | Wolf et al. | 600/300 |
| 2007/0213658 A1 | 9/2007 | Hickle | |
| 2007/0213684 A1 | 9/2007 | Hickle et al. | |
| 2009/0118697 A1 | 5/2009 | Martin | |
| 2009/0133699 A1 | 5/2009 | Nalagatla et al. | |
| 2009/0292179 A1 | 11/2009 | Jampala et al. | |
| 2009/0292226 A1 | 11/2009 | Feng et al. | |
| 2010/0010321 A1 | 1/2010 | Foster | |
| 2010/0010433 A1 | 1/2010 | Krough et al. | |
| 2010/0069438 A1 | 3/2010 | Hickle | |
| 2010/0179854 A1 | 7/2010 | Shafer et al. | |
| 2010/0300438 A1 | 12/2010 | Martin et al. | |
| 2011/0021978 A1 | 1/2011 | Martin et al. | |
| 2011/0040158 A1 | 2/2011 | Katz et al. | |
| 2011/0119612 A1 | 5/2011 | Gannon et al. | |
| 2011/0152629 A1 | 6/2011 | Eaton et al. | |
| 2011/0245579 A1 | 10/2011 | Bruggeman et al. | |
| 2012/0010591 A1 | 1/2012 | Chazot et al. | |
| 2013/0046197 A1 | 2/2013 | Dlugos, Jr. et al. | |
| 2013/0046279 A1 | 2/2013 | Niklewski et al. | |
| 2013/0046280 A1 | 2/2013 | Martin et al. | |

FOREIGN PATENT DOCUMENTS

| | | |
|---|---|---|
| EP | 0796590 | 9/1997 |
| EP | 1547631 | 6/2005 |
| WO | WO 03/030979 | 4/2003 |
| WO | WO 2005/061028 | 7/2005 |
| WO | WO 2010/081947 | 7/2010 |

OTHER PUBLICATIONS

European Search Report dated Jul. 25, 2013 for Application No. 12180550.1.
European Search Report dated Jul. 30, 2013 for Application No. 12180541.0.
European Search Report dated Aug. 2, 2013 for Application No. 12180544.4.
Office Action Non-Final dated Jan. 10, 2013 for U.S. Appl. No. 13/210,517.
Office Action Final dated Jul. 11, 2013 for U.S. Appl. No. 13/210,517.
Restriction Requirement dated Aug. 28, 2013 for U.S. Appl. No. 13/210,530.
Office Action Non Final dated Apr. 16, 2013 for U.S. Appl. No. 13/210,540.
New Zealand Examination Report dated Aug. 20, 2012 for Application No. 601828.
New Zealand Examination Report dated Aug. 21, 2012 for Application No. 601831.
New Zealand Examination Report dated Aug. 21, 2012 for Application No. 601833.
New Zealand Examination Report dated Aug. 21, 2012 for Application No. 601834.
Restriction Requirement dated Nov. 15, 2012 for U.S. Appl. No. 13/210,517.
Restriction Requirement dated Nov. 16, 2012 for U.S. Appl. No. 13/210,540.
Non-Final Rejection dated Jan. 16, 2014 for U.S. Appl. No. 13/210,530.
Final Rejection dated Nov. 22, 2013 for U.S. Appl. No. 13/210,540.
European Communication dated Apr. 17, 2014 for Application No. EP 12180546.9.
New Zealand First Examination Report dated Feb. 20, 2014 for Application No. 621169.
New Zealand First Examination Report dated Feb. 20, 2014 for Application No. 621171.
New Zealand First Examination Report dated Feb. 21, 2014 for Application No. 621225.
New Zealand Further Examination Report dated Feb. 21, 2014 for Application No. 601828.
New Zealand Further Examination Report dated Mar. 4, 2014 for Application No. 601831.
Non-Final Office Action dated Jul. 3, 2014 for U.S. Appl. No. 13/210,517.
Final Office Action dated Jul. 11, 2014 for U.S. Appl. No. 13/210,530.
Office Action, Final, dated Nov. 26, 2014 for U.S. Appl. No. 13/210,517.

* cited by examiner

DRUG DELIVERY SYSTEM WITH OPEN ARCHITECTURAL FRAMEWORK

BACKGROUND

Patient monitoring systems may be used to monitor physiological parameters of patients undergoing diagnostic procedures, surgical procedures, and/or various other types of medical procedures. In some settings, a nurse or technician in a pre-procedure room may prepare a patient for an upcoming procedure. This preparation may include connecting monitors to the patient for the purpose of obtaining baseline data to be used in the procedure. Such monitors may include a blood pressure monitor and pulse oximetry monitor, among others. Blood pressure readings may be taken by a blood pressure cuff, whereby a nurse or technician secures the cuff around a patient's arm and uses a device to pump air into the cuff. Once the reading from the cuff stabilizes, the nurse or technician may have to manually record the data (e.g., handwritten on a sheet of paper or typed into a portable electronic device), and save this information for later reference during the procedure and eventually, for a patient report. For the nurse or technician to take a pulse oximeter reading, he or she may have to boot up the pulse oximeter module, secure a pulse oximeter probe upon the patient, and take a reading of the patient. This reading may also be written down on paper or otherwise be manually recorded for later use. Once it is determined the patient is ready for the procedure, the nurse or technician may have to disengage the blood pressure cuff and pulse oximetry probes from the patient, so the patient can be transported from the pre-procedure room to the procedure room.

After the patient enters the procedure room and before the procedure begins, several tasks may be needed to prepare the patient for the procedure. The nurse or technician may have to reconnect both blood pressure and pulse oximetry readers before the procedure can begin. In addition to blood pressure and pulse oximetry, other connections such as, for example, capnography, supplemental oxygen, and electrocardiogram may be required. A great deal of time may be required to connect the physiological monitors to the patient and to connect the physiological monitors to the monitoring system. In some such instances, the nurse or technician must spend time reconnecting the same kinds of physiological monitors that were previously connected to the patient in the pre-procedure room. The time it takes to make these connections may occupy valuable procedure room time, thus decreasing practice efficiency. It may therefore be desirable to minimize or eliminate these monitor connections and reconnections while the patient is in the procedure room.

In various settings, it may also be desirable to deliver drugs to a patient during a procedure, such as via an IV and/or face mask, etc. Such drugs may include sedatives, anelgesics, amnestics, etc. In some instances, such drugs may be selected and/or combined to place a patient in a state of "conscious sedation" (in lieu of simply rendering a patient completely unconscious through a general anesthetic). Certain systems may also be used to automate the delivery of such drugs. For instance, such systems may be located in the same room where a medical procedure is performed, and may be coupled with a physiological monitoring system to automatically tailor the delivery of drugs based on patient parameters detected by the monitoring system. Examples of such systems are disclosed in U.S. Pat. No. 6,745,764, entitled "Apparatus and Method for Providing a Conscious Patient Relief from Pain and Anxiety Associated with Medical or Surgical Procedures," issued Jun. 8, 2004, the disclosure of which is incorporated by reference herein; U.S. Pat. No. 7,833,213, entitled "Patient Monitoring and Drug Delivery System and Method," issued Nov. 16, 2010, the disclosure of which is incorporated by reference herein; U.S. Pat. No. 7,935,081, entitled "Drug Delivery Cassette and a Medical Effector System," issued May 3, 2011, the disclosure of which is incorporated by reference herein; U.S. Pub. No. 2009/0292179, entitled "Medical System having a Medical Unit and a Display Monitor," published Nov. 26, 2009, the disclosure of which is incorporated by reference herein; and U.S. Pub. No. 2010/0010433, entitled "Medical System which Controls Delivery of a Drug," published Jan. 14, 2010, the disclosure of which is incorporated by reference herein.

While a variety of systems have been made and used for monitoring patients and delivering drugs to patients, it is believed that no one prior to the inventor(s) has made or used the technology as described herein.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
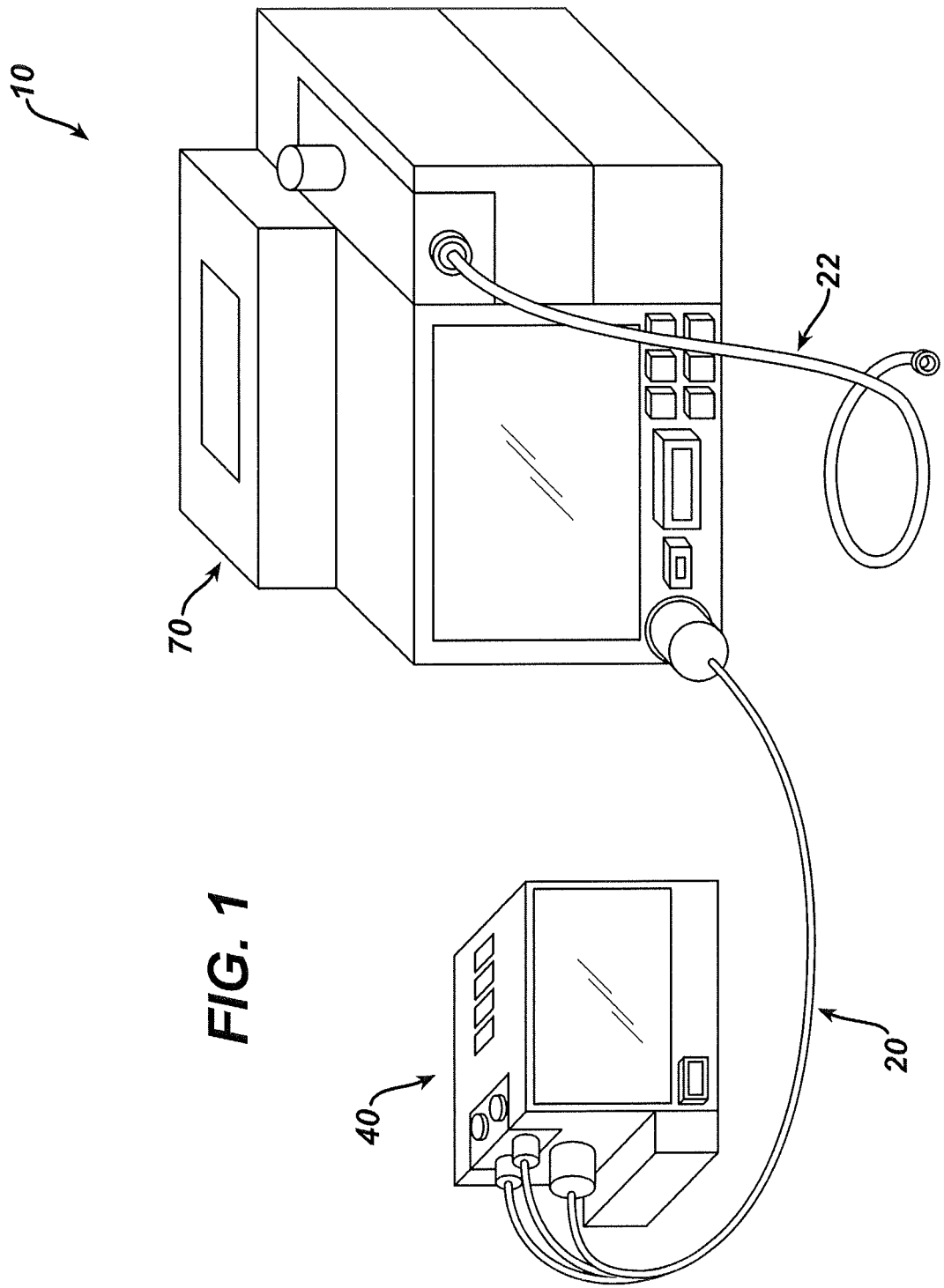
FIG. 1 depicts a perspective view of an exemplary patient monitoring and drug delivery system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It should further be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview

FIG. 1 shows an exemplary patient care system (10) comprising a bedside monitor unit (BMU) (40) and a procedure room unit (PRU) (70). One exemplary use of patient care system (10) is to monitor patient parameters and deliver sedative, analgesic, and/or amnestic drugs to a conscious, non-intubated, spontaneously-ventilating patient undergoing a diagnostic procedure, surgical procedure, or other medical procedure by a physician. This use is not exhaustive of all of the potential uses of the invention but will be used to describe examples herein. BMU (40) and PRU (70) are connected via communication cable (20). Communication cable (20) provides means for transmitting electronic data as well as various hydraulic signals and gases between BMU (40) and PRU (70). For instance, communication cable (20) may include a plurality of pneumatic tubes and a plurality of electrical wires, all integrated within a single sheath or cable. Communication cable (20) may be removed from both BMU (40) and PRU (70) to facilitate practice efficiency and user convenience. BMU (40) and PRU (70) are free to move independently of each other if communication cable (20) is not in place. This allows for mobility of each unit independent of the other; this feature is especially important in hospitals that have a great deal of medical procedures and there is little time to connect patients to monitors. BMU (40) and PRU (70) preferably accommodate an external oxygen source that is intended to provide supplemental oxygen to the patient during the course of a surgical procedure if the clinician so desires. An IV tube set (22) is shown connected to PRU (70) and delivers sedative or amnestic drugs to a patient during a surgical procedure.

Figure 2:
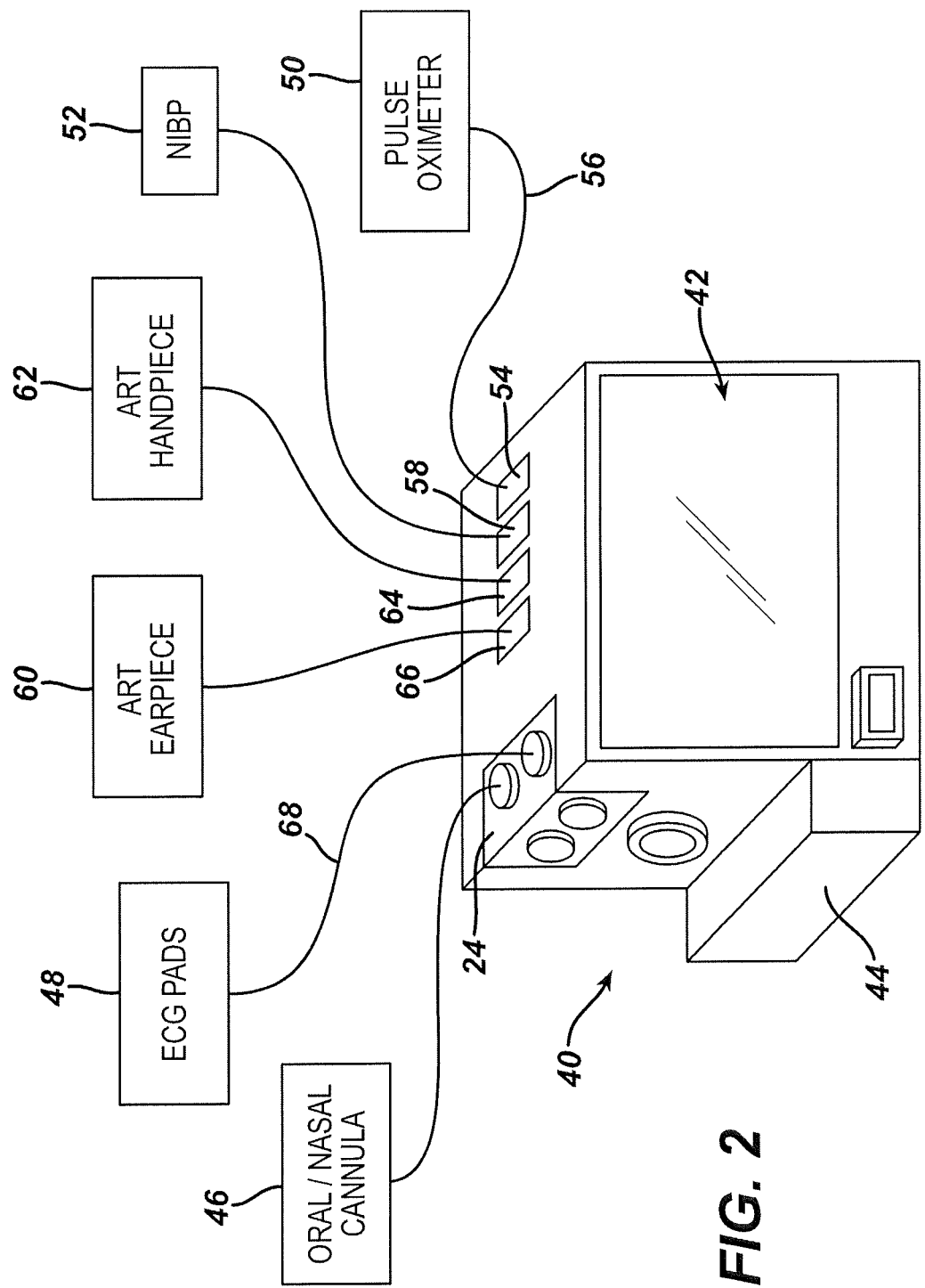
FIG. 2 depicts a perspective view of the patient monitoring unit of the system of FIG. 1.

BMU (40) serves as a patient monitoring unit, monitoring various physiological parameters of a patient. As shown in FIG. 2, BMU (40) is compact and portable so it requires relatively little effort to move from one room to another. In some versions, BMU (40) could mount upon either an IV pole or a bedrail; this would free the clinician from the burden of carrying the unit wherever the patient needs to be transported. BMU (40) is small and light enough to be held in the hand of a nurse or technician. BMU (40) allows the user to input information via a touch screen assembly (42) or a simple keypad, etc. Touch screen assembly (42) is provided as an overlay on a display device that is integrated into one surface of BMU (40), and that displays patient and system parameters, and operational status of BMU (40). An exemplary bedside touch screen assembly (42) is a 5.25" resistive touch screen manufactured by MicroTech mounted upon a 5.25" color LCD screen manufactured by Samsung. Other suitable forms that a display screen and touch screen may take will be apparent to those of ordinary skill in the art in view of the teachings herein. An attending nurse or physician may enter patient information such as, for example, patient weight and a drug dose profile into BMU (40) by means of bedside touch screen assembly (42). A BMU battery (44) is fixedly attached to the BMU (40) and comprises a standard rechargeable battery such as, for example, Panasonic model no. LC-T122PU, that is capable of supplying sufficient power to run BMU (40) for an extended period of time. In some versions, BMU battery (44) can be recharged while BMU (40) is connected to PRU (70) via communication cable (20) or can be charged directly from an independent power source. Various suitable ways in which battery (44) may be charged will be described in greater detail below in section III.A.; while still other suitable ways will be apparent to those of ordinary skill in the art in view of the teachings herein. Similarly, various suitable forms that battery (44) may take, as well as various suitable compositions thereof, will be apparent to those of ordinary skill in the art in view of the teachings herein.

As shown in FIG. 2, BMU (40) may be connected to a plurality of patient sensors and peripherals used to monitor patient vital signs and deliver supplemental oxygen to the patient. Oral nasal cannula (46) delivers oxygen from an external oxygen source and collects samples of exhaled gas. Oral nasal cannula (46) is removably attached to cable pass-through connection (24). Cable pass-through connection (24) sends the signal obtained by oral nasal cannula (46) directly to a capnometer (e.g., a CardioPulmonary Technologies CO2WFA OEM) in PRU (70) and preferably via communication cable (20) (FIG. 1). The capnometer measures the carbon dioxide levels in a patient's inhalation/exhalation stream via a carbon dioxide-sensor as well as measuring respiration rate. Also attached to the cable pass-through connection (24) is a standard electrocardiogram (ECG) (48), which monitors the electrical activity in a patient's cardiac cycle. The ECG signals are sent to the PRU (70) where the signals are processed. A pulse oximeter probe (50) (e.g., by Dolphin Medical) and a non-invasive blood pressure (NIBP) cuff (52) are also connected to BMU (40) in the present example. Pulse oximeter probe (50) measures a patient's arterial saturation and heart rate via an infrared diffusion sensor. The data retrieved by pulse oximeter probe (50) is relayed to pulse oximeter module (54) (e.g., by Dolphin Medical) by means of pulse oximeter cable (56). The NIBP cuff (52) (e.g., a SunTech Medical Instruments PN 92-0011-00) measures a patient's systolic, diastolic, and mean arterial blood pressure by means of an inflatable cuff and air pump (e.g., by SunTech Medical), also incorporated as needed. NIBP cuff (52) is removably attached to NIBP module (58) located on BMU (40).

In the present example, a patient's level of consciousness is detected by means of an Automated Response Tester System (ART), though like various other components described herein, an ART system is merely optional and is not required. An exemplary ART system is disclosed in U.S. Pub. No.

2005/0070823, entitled "Response Testing for Conscious Sedation Involving Hand Grip Dynamics," published Mar. 31, 2005, the disclosure of which is incorporated by reference herein. The ART system of the present example comprises a query initiate device and a query response device. The ART system operates by obtaining the patient's attention with the query initiate device and commanding the patient to activate the query response device. The query initiate device may comprise any type of stimulus device such as a speaker via an earpiece (60), which provides an auditory command to a patient to activate the query response device. The query response device of the present example comprises is a handpiece (62) that can take the form of, for example, a toggle or rocker switch or a depressible button or other moveable member hand held or otherwise accessible to the patient so that the member can be moved or depressed by the patient upon the patient's receiving of the auditory signal or other instruction to respond. Alternatively, a vibrating mechanism may be incorporated into handpiece (62) that cues the patient to activate the query response device. For instance, in some versions, the query initiate device comprises a cylindrical handheld device (62), containing a small 12V DC bi-directional motor enabling the handheld device to vibrate the patient's hand to solicit a response.

After the query is initiated, the ART system generates signals to reflect the amount of time it took for the patient to activate the query response device in response to the query initiate device. These signals are processed by a logic board located inside BMU (40) and are displayed upon either bedside touch screen assembly (42), procedure touch screen assembly (72) (FIG. 3), and/or an optional monitor 104 (FIG. 4). The amount of time needed for the patient to respond to the query gives the clinician an idea as to the sedation level of the patient. The ART system has two modules in this example, including a query response module (64) and a query initiate module (66), collectively referred to as the ART system modules (64, 66). ART system modules (64, 66) have all the necessary hardware to operate and connect the query response device (62) and the query initiate device (60) to BMU (40).

In some versions monitoring modules (54, 58, 64, 66) are easily replaceable with other monitoring modules in the event of malfunction or technological advancement. These modules (54, 58, 64, 66) include all of the necessary hardware to operate their respective peripherals. The above-mentioned patient modules (54, 58, 64, 66) are connected to a microprocessor-based electronic controller or computer (MLB) located within each of the PRU (70) and BMU (40). The electronic controller or main logic board comprises a combination of available programmable-type microprocessors and other "chips," memory devices and logic devices on various board(s) such as, for example, those manufactured by Texas Instruments (e.g., XK21E) and National Semiconductor (e.g., HKL72), among others. Various other suitable forms that modules (54, 58, 64, 66) and associated electronics may take will be apparent to those of ordinary skill in the art in view of the teachings herein.

Once BMU (40) and PRU (70) are connected via communication cable (20), ECG and capnography may be monitored, and supplemental oxygen may be delivered to the patient. It should be understood, however, that these connections may be made in the pre-procedure room to increase practice efficiency. By making these connections in the pre-procedure room, less time may be required in the procedure room connecting capnography, ECG and supplemental oxygen to PRU (70). Oral nasal cannula (46) and ECG leads (68) are connected directly to cable pass-through connection (24).

Cable pass-through connection (24), located on BMU (40), is essentially an extension of communication cable (20), which allows the signals from ECG leads (68) and oral nasal cannula (46) to bypass BMU (40) and be transferred directly to PRU (70). It will be evident to those skilled in the art, however, that the BMU (40) could be configured to accept the ECG (48) and oral/nasal cannula (46) signals and process the signals accordingly to provide the information on screen (42) and supplemental oxygen to the patient in the pre-procedure room. Other examples of components, features, and functionality that may be incorporated into BMU (40) will be described in greater detail below; while still further examples of components, features, and functionality that may be incorporated into BMU (40) will be apparent to those of ordinary skill in the art in view of the teachings herein.

Figure 3:
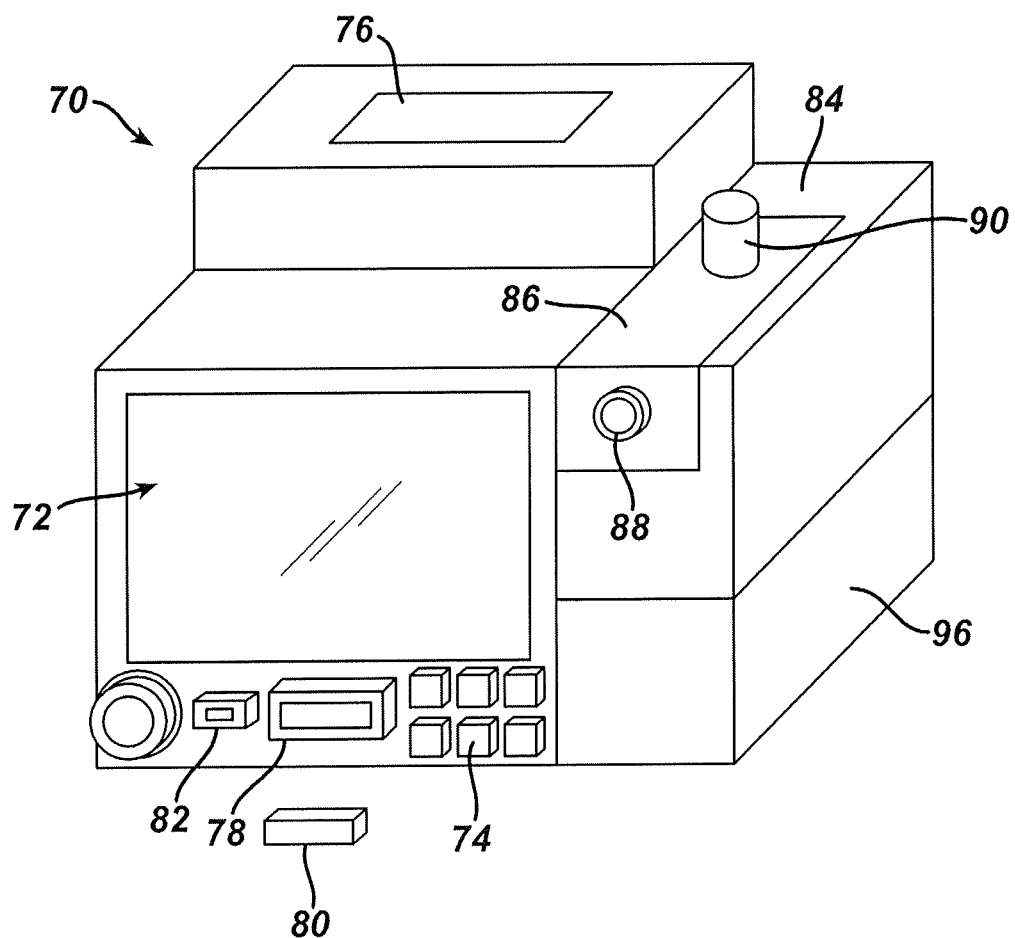
FIG. 3 depicts a perspective view of the drug delivery unit of the system of FIG. 1.
Figure 4:
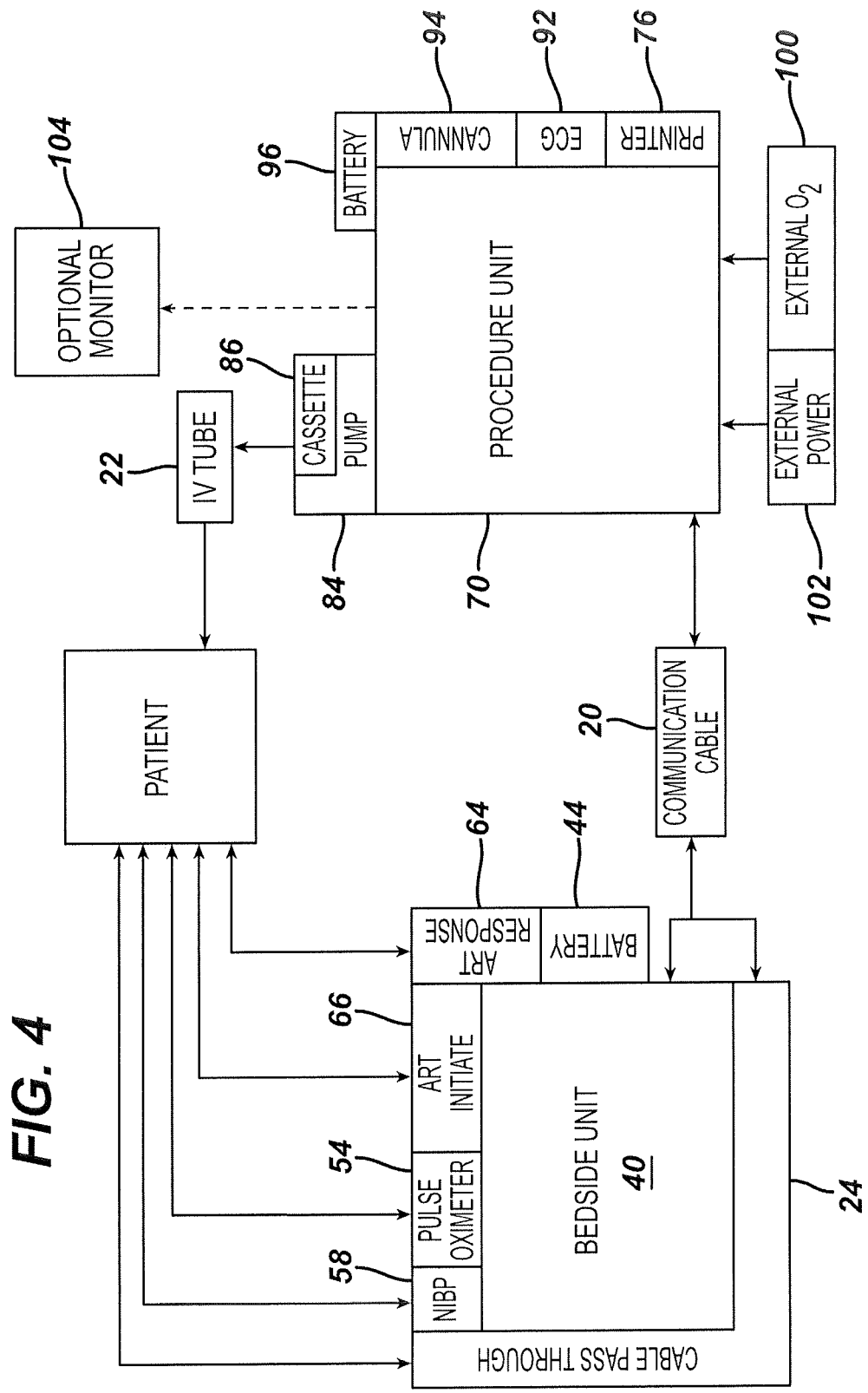
FIG. 4 depicts a block diagrammatic view of the system of FIG. 1 with additional exemplary components.

Referring now to FIG. 3, PRU (70) allows a physician to safely deliver drugs, such as sedative, analgesic, and/or amnestic drugs to a patient, and monitor the patient during a medical procedure. Procedure touch screen assembly (72) comprises a display device that is integrated into the surface of PRU (70), which displays patient and system parameters, and operation status of PRU (70). In some versions, procedure touch screen assembly (72) comprises a 15" resistive touch screen manufactured by MicroTech mounted upon a 15" color LCD screen manufactured by Samsung. Other suitable forms that a display screen and touch screen may take will be apparent to those of ordinary skill in the art in view of the teachings herein. It should be noted that, in the present example, procedure touch screen assembly (72) is the primary display and user input means, and is significantly larger than the bedside touch screen assembly (42) and is capable of displaying more detailed information. In addition to procedure touch screen assembly (72), the user may input information into PRU (70) by means of drug delivery controls (74). Drug delivery controls (74), such as buttons, dials, etc., are located on one side of PRU (70) and allow the clinician to change various system parameters and bypass procedure touch screen assembly (72). A printer (76) is integrally attached to the top of PRU (70). Printer (76) allows the clinician to print a patient report that includes patient data for pre-op and the procedure itself. The combination of printing a patient report and the automatic data logging features may decrease the amount of time and effort a nurse or technician must spend regarding patient condition during the course of a procedure. Printer (76) receives data signals from a printer interface (e.g., Parallel Systems CK205HS), which is located on the main logic board. Printer (76) may comprise a thermal printer (e.g., Advanced Printing Systems (APS) ELM 205HS) and/or any other suitable type of printer. It should also be understood that printer (76) may be remote from PRU (70) and may even be omitted altogether, if desired.

Memory card reader (78), which includes a slot in the outer casing of PRU (70), allows flash memory card (80) to be inserted and removed from PRU (70). Flash memory card (80) is a solid-state storage device used for easy and fast information storage of the data log generated by PRU (70). The data is stored so that it may be retrieved from flash memory card (80) at a later time. In some versions, memory card reader (78) accepts flash memory card (80) containing software to upgrade the functionality of patient care system (10). Again, as with other components described herein, memory card reader (78) may be modified, substituted, supplemented, or omitted as desired. In the present example, memory card reader (78) is supplemented with a data port (82). Data port (82) may include, but is not limited to, a standard serial port, a USB port, a RS232 port, an Ethernet port, or a wireless adapter (e.g., using IEEE 802.11n/g/b/a standard, etc.). Data port (82) may be used to link PRU (70) to an external printer to print a patient report or to transfer electronic files to a personal computer or mainframe. A merely illustrative example of how data port (82) may be used to communicate with a centralized network system component will be described in greater detail below in section III. B., while still other suitable examples will be apparent to those of ordinary skill in the art in view of the teachings herein.

PRU (70) delivers fluid to a patient via an infusion pump, such as a peristaltic infusion pump (84) (e.g., by B-Braun McGaw). Peristaltic infusion pump (84) is integrally attached to PRU (70), and uses peristaltic fingers to create a wavelike motion to induce fluid flow inside a flexible tube connected to a fluid reservoir. A drug cassette (86) is a generally rectangular shaped structure that is placed adjacent to peristaltic infusion pump (84). Drug cassette (86) of this example is made of a rigid thermoplastic such as, for example, polycarbonate. Drug cassette (86) has an internal cavity that houses IV tubing (22) made of a flexible thermoplastic such as, for example, polypropylene (e.g., Kelcourt). Drug cassette (86) receives tubing (22) via a port (88) and accurately and reliably positions exposed IV tubing (22) in contact with the peristaltic fingers of peristaltic infusion pump (84). IV tube set (22) attaches to a fluid vial (90), and a portion of the length of IV tube set (22) is contained within drug cassette (86). Another portion of IV tube set (22) lies external to drug cassette (86) to facilitate the interaction with peristaltic pump (84). IV tubing (22) is coiled within drug cassette (86) and has a length to reach a patient removed from the PRU (70). A fluid detection sensor (not shown) may be mounted to an inner wall of drug cassette (86). Such a fluid detection sensor may comprise any one of known fluid sensors, such as the MTI-2000 Fotonic Sensor, or the Microtrak-II CCD Laser Triangulation Sensor both by MTI Instruments Inc. IV tube set (22) may run through the fluid detection sensor before exiting drug cassette (86). PRU (70) may include features operable to prime IV tubing (22) with relative ease for a user. Various examples of how such priming may be provided are disclosed in U.S. Pat. No. 7,833,213, the disclosure of which is incorporated by reference herein.

In the present example, drug cassette (86) includes just one vial (90). However, it should be understood that some versions of drug cassette (86) may include several vials (90). Such vials (90) may include the same drug. Alternatively, a plurality of vials (90) associated with a single drug cassette (86) may include a variety of different kinds of drugs. In other words, a single drug cassette (86) may be used to selectively deliver two or more drugs simultaneously and/or in a particular sequence. While vials (90) are used in the present example, it should be understood that any other suitable type of container may be used as will be understood by those of ordinary skill in the art in view of the teachings herein. It should also be understood that some versions of PRU (70) may be configured to receive two or more drug cassettes (86). Each such drug cassette (86) may be associated with a single drug (e.g., different drug cassettes (86) used for different drugs), or each drug cassette (86) may be associated with a combination of drugs (e.g., different drug cassettes (86) used for different combinations of drugs).

FIG. 4 shows how components of system (10) interface with each other and with a patient. While not shown in FIG. 3, FIG. 4 shows how PRU (70) includes an integral ECG module (92) and integral cannula module (94). ECG module (92) is coupled with ECG (48) via ECG leads (68) extending from pass-through connection (24). Cannula module (94) is coupled with oral/nasal cannula (46), also through pass-through connection (24). Like modules (54, 58, 64, 66) described above, modules (92, 94) may be easily replaceable with other monitoring modules in the event of malfunction or technological advancement. Modules (92, 94) may also include all of the necessary hardware to operate their respective peripherals, and may be further coupled with a microprocessor-based electronic controller or computer located within PRU (70) and/or BMU (40).

As also shown in FIG. 4, PRU (70) of the present example is coupled with an external oxygen source (100), an external power source (102), and an external monitor (104). External oxygen source (100) may by regulated by one or more components of PRU (70), which may deliver oxygen from oxygen source (100) to the patient based on one or more parameters sensed by BMU (40), based on drug delivery from cassette (86), and/or based on other factors. External power source (102) may be used as a primary source of power for PRU (70), with a battery (96) being used as a backup power source. Alternatively, battery (96) may be used as a primary source of power for PRU, with external power source (102) being used for backup power and/or to charge battery (96). External monitor (104) may be used to supplement or to substitute the display features of touch screen assembly (42) and/or touch screen assembly (72). For instance, external monitor (104) may display information including patient physiological parameters, status of operation of system (10), warning alerts, etc. PRU (70) and/or BMU (40) may communicate with external monitor (104) via cable, wirelessly (e.g., via RF transmission, etc.), or otherwise. Other examples of components, features, and functionality that may be incorporated into PRU (70) will be described in greater detail below; while still further examples of components, features, and functionality that may be incorporated into PRU (70) will be apparent to those of ordinary skill in the art in view of the teachings herein.

Figure 5:
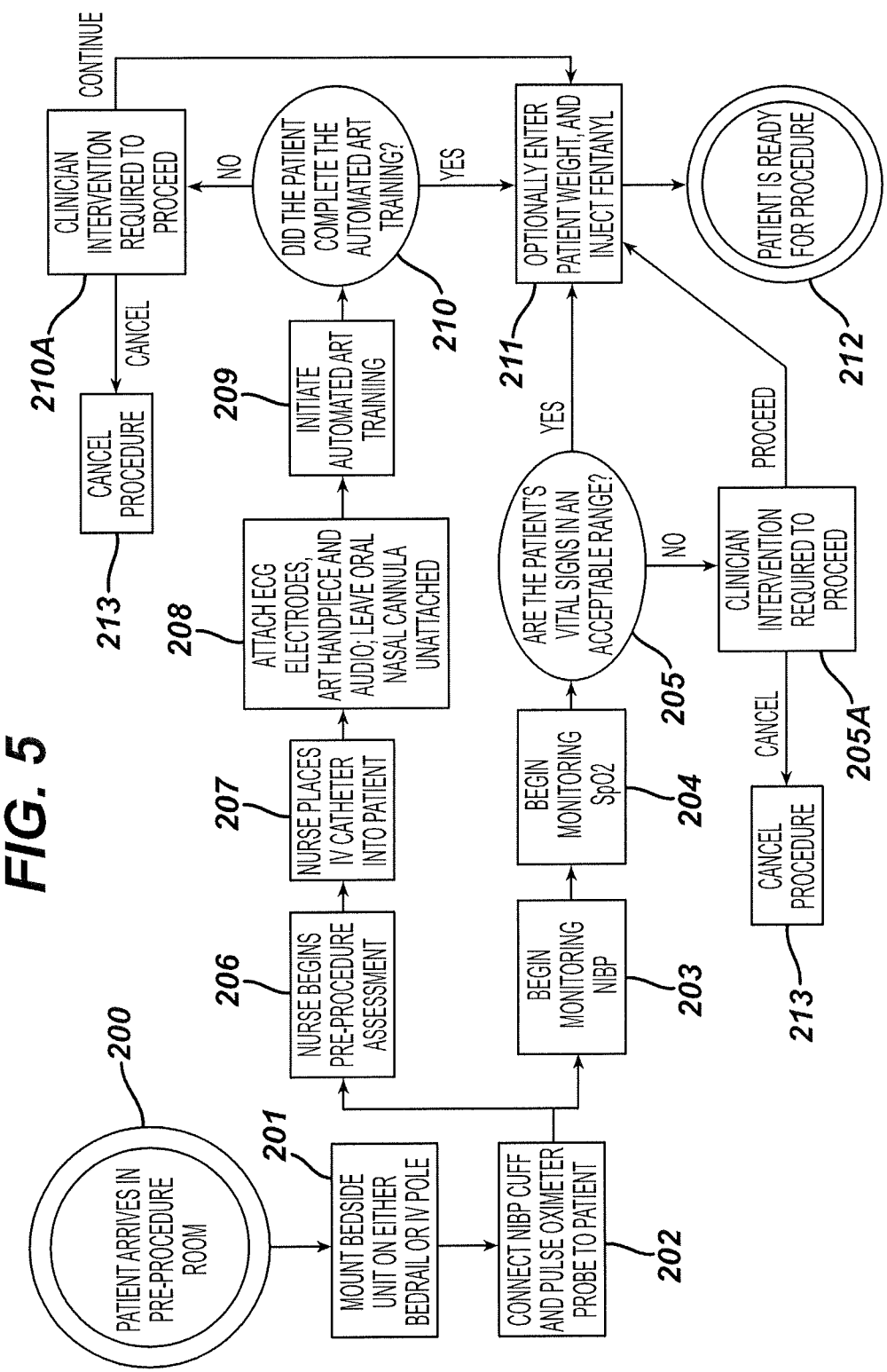
FIG. 5 depicts a flow diagram of an exemplary process that may be carried out before a medical procedure, using the patient monitoring unit of FIG. 2.

FIG. 5 shows a data flow diagram outlining an exemplary process of a pre-procedure room, though it should be understood that system (10) may be used in various other ways. As shown, the patient arrives in the pre-procedure room, step (200). A nurse or technician mounts BMU (40) to either the bedrail or IV pole, (step 201). BMU (40) of the present example is equipped with an IV pole clamp or a quick connect to quickly and easily mount the unit on either the bedrail or IV pole. Once BMU (40) is in place, the nurse or clinician may connect NIBP cuff (52) and pulse oximeter probe (50) to the patient, step (202). These connections are made between the patient and BMU (40). BMU (40) will automatically begin monitoring parameters such as, for example, diastolic and systolic blood pressure, mean arterial pressure, pulse rate, oxygenation plethysmogram, and oximetry value, steps (203, 204). The readings taken by BMU (40) will be displayed for the nurse or technician on bedside touch screen assembly (42). While patient parameters are being monitored, the nurse or technician is free to perform other tasks. For instance, the nurse or technician may need to complete a pre-procedure assessment, step (206). The pre-procedure assessment may include recording patient vital signs, determining any known allergies, and determining patient's previous medical history. Once the nurse or technician has completed the pre-procedure assessment, step (206), the nurse or technician may start the peripheral IV by placing a catheter in the patient's arm, step (207). The IV catheter is connected to the primary IV drip device such as, for example, a 500 mL bag of saline fluid. Upon completion of the above activities, the nurse or technician begins to attach ECG pads (48), ART handpiece (62), ART earpiece (60) and oral nasal cannula (46) to the patient, step (208). In some versions, patient care system (10) has the capability to automatically detect and recognize the proper connection of the monitors when they are connected from the patient to BMU (40).

Once the patient is connected to the above-mentioned items, the nurse or technician may explain the ART system to the patient. This explanation may involve the nurse or technician instructing the patient to respond to auditory stimulation from ART earpiece (60) and/or tactile stimulation from ART handpiece (62) by squeezing ART handpiece (62). If the patient fails to respond to either auditory or tactile stimulation, the intensity of the stimulation will increase until the patient responds successfully. At this point, the nurse may initiate an automated ART training, step (209). Automated ART training is a program run by BMU (40) that teaches the patient how to detect an ART stimulus and how to respond to that stimulus and sets a baseline patient response to the stimulus as disclosed in the previously referenced U.S. Pub. No. 2005/0070823. The nurse or technician is free to perform other patient related tasks while the patient is participating in the automated ART training. BMU (40) will display the automated ART training status via touch screen assembly (42) so the nurse or technician can quickly determine if the patient is participating in the automated training. The patient must successfully complete the automated ART training to proceed, step (210). If the patient fails to complete the training a nurse or other clinician must intervene and determine if the patient may continue, step (210A). If the clinician decides the user may proceed, then the patient will proceed to step (211). If the clinician decides the patient is unable to continue, then the procedure will be canceled, step (213). The user may customize the automated ART training to automatically repeat at specified intervals (e.g., 10 minutes) if the patient is required to wait to enter the procedure room. This may help to instill the newly learned response.

In addition to successfully completing automated ART training, the patient's parameters must be in an acceptable range, step (205). The clinician may decide upon what an acceptable range is by inputting this information into BMU (40) by means of bedside touch screen assembly (42). If any one of the parameters being monitored falls outside a given range, the patient will not be permitted to undergo a procedure until a nurse or other clinician examines the patient to determine whether or not the patient may continue, step (205A). If the clinician decides the patient is able to continue, the patient will proceed to step (211), if the clinician decides the patient is unable to continue, then the procedure will be cancelled, step (213). Just prior to leaving the pre-procedure room for the procedure room, the nurse administers a predetermined low dose of an analgesic drug, step (211) such as, for example, a 1.5 mcg/kg of Fentanyl. After the injection of the analgesic drug, the patient is ready to be moved to the procedure room, step (212).

Figure 6:
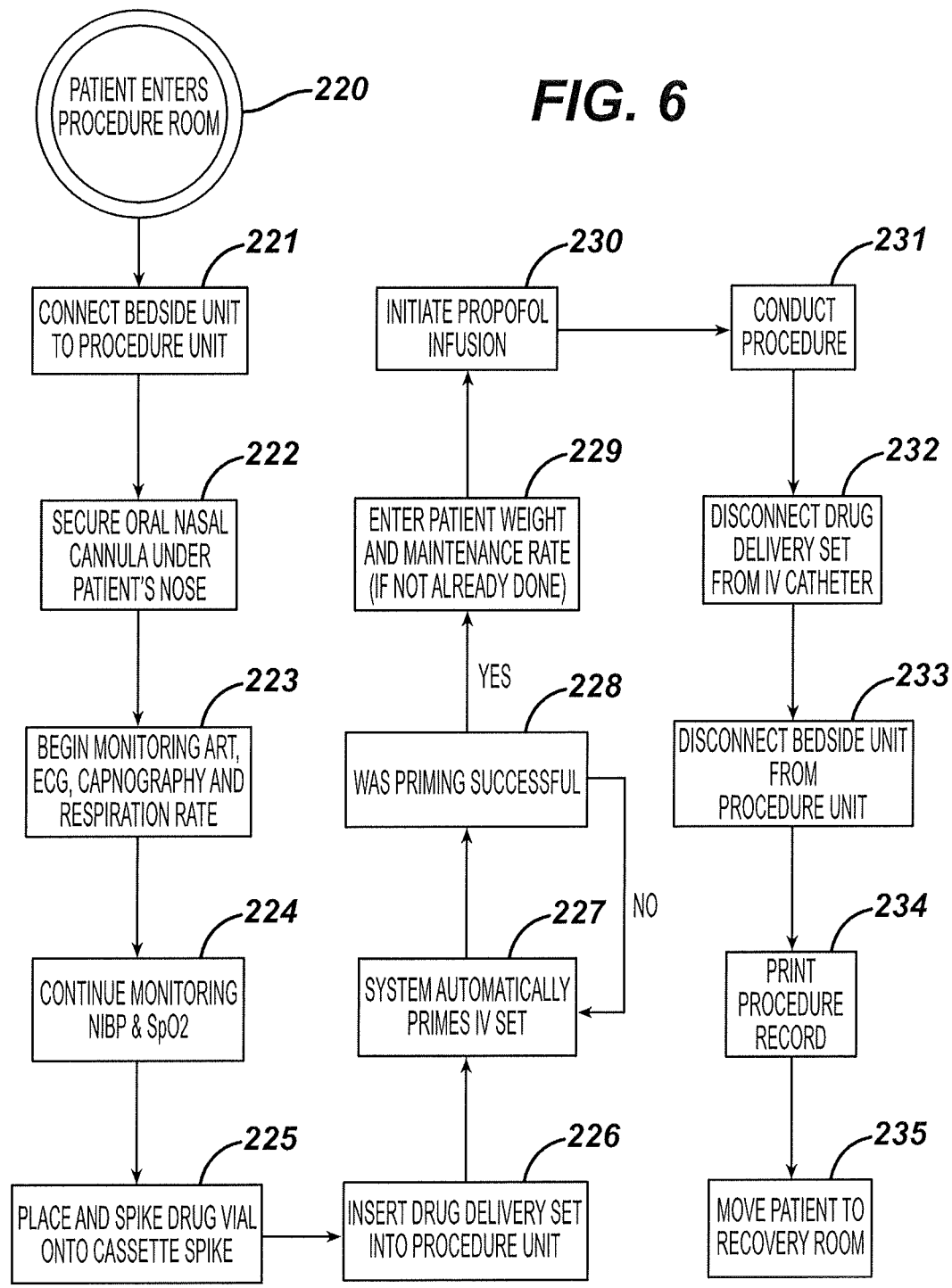
FIG. 6 depicts a flow diagram of an exemplary process that may be carried out during a medical procedure, using the system of FIG. 1.

FIG. 6 is a flow chart illustrating an exemplary use of system (10) while the patient is in the procedure room, though it should be understood that system (10) may be used in various other ways. As shown, the patient and BMU (40) are moved into the procedure room, step (220) and are received by the physician and procedure nurse. BMU (40) may be connected to PRU (70) via cable (20) upon the patient entering the procedure room, step (221). Upon connection, the NIBP, pulse and oximetery history from the patient will automatically upload from BMU (40) to PRU (70), displaying patient history for the last period of monitoring. In addition to NIBP and pulse oximeter history, a record verifying the patient has completed ART training will also be uploaded. Upon connection of BMU (40) to PRU (70), the small display (42) on BMU (40) changes immediately from a monitoring screen to a remote entry screen for PRU (70). Display information from BMU (40) is automatically transferred to PRU (70). Of course, in some versions displays (42, 72) may simultaneously display different information, and either or both may accept different kinds of touch inputs, etc.

At this point, the procedure nurse may secure oral nasal cannula (46) to the patient's face, step (222). PRU (70) may begin monitoring patient parameters such as, for example, ART, ECG, and capnography now that all connections between the patient and PRU (70) are complete, step (223). PRU (70) will continue monitoring patient parameters such as, for example, NIBP, pulse, and oximetery, step (224). Next, the procedure nurse may place and spike a standard drug vial (90), step (225) onto drug cassette (86). Drug cassette (86) of the present example has an integral, cannulated drug vial spike that serves to puncture the rubber vial stopper and allow fluid from the drug vial (90) to enter drug cassette (86). Next, the procedure nurse places drug cassette (86) adjacent to peristaltic infusion pump (84) making sure that the exposed portion of IV tubing (22) lines up with the peristaltic fingers, step (226). Once the fluid vial (90) and drug cassette (86) are loaded correctly, the nurse may autoprime IV tubing (22). In some versions, the procedure nurse would press a button located upon PRU (70) to initiate the autopriming, step (227), thereby automatically purging air from IV tubing (22). PRU (70) continuously monitors the autopriming process to determine the overall success of the autopriming. If PRU (70) fails to properly purge IV tubing (22), a warning notification is made to the user so that the procedure nurse may repeat the autopriming sequence until IV tubing (22) is successfully purged, step (227).

Upon successful completion of the autopriming sequence, the procedure nurse may enter the patient weight in pounds while the physician may enter the initial drug maintenance dose rate as well as dose method (e.g., normal or rapid infusion), step (229). After the patient weight and dose rate have been inputted, the physician or procedure nurse may initiate drug infusion, step (230). While the drug is taking effect upon the patient, the physician may perform standard procedure related activities such as, for example, test a viewing scope, and apply any topical anesthetic. Once the drug has taken the desired effect upon the patient, the physician and procedure nurse are free to conduct the procedure, step (231). Upon completion of the procedure, the clinician may disconnect the drug delivery cassette (86) from the IV tubing (22), step (232) and disconnect BMU (40) from PRU (70), step (233). If the clinician so desires, PRU (70) may print a record of the patient's physiological parameters from printer (76) at this time, step (234). The printout of the procedure record may include patient monitoring data such as, for example, NIPB, pulse oximetery, capnography, respiration rate, and heart rate. Other system events that may be included in the print out include ART competency, ART responsiveness during the procedure, oxygen delivery history, drug dose, monitoring intervals, drug bolus amount and time, and total drug volume delivered during the procedure. The printout may include a section where the procedure nurse may enter in notes of her own, such as, for example, additional narcotic delivered, topical spray used, Ramsey Sedation Scale, procedure start and finish time, cautery unit and settings used, cautery grounding site, dilation equipment type and size, and Aldrete Score, etc. After printing the patient record, the patient may then be moved to the recovery room, step (235).

At one or more stages of a procedure when system (10) is being used, such as steps (230, 231) described above, PRU (70) may automatically regulate the delivery of one or more drugs to the patient. Such regulation of drug delivery may be based on patient physiological data from BMU (40), based on other data input into BMU (40) and/or into PRU (70), and/or based on selections made by a physician or other user of system (10) (e.g., indicating the type of medical procedure, the type of drug(s) in cassette (86), etc.). In some versions, the regulation of drug delivery by PRU (70) may be dynamic and may change in real time during a medical procedure, based on detected changes in patient physiological data, etc. PRU (70) and/or BMU (40) may also provide alerts to a physician or other user of system (10) during a medical procedure, based at least in part on on patient physiological data from BMU (40), etc. Such drug delivery responses and alert responses may be provided in accordance with a "safety shell" control algorithm executed through a control logic in PRU (70). In some versions, a safety shell provides fully automated drug delivery to the patient from PRU (70), based on conditions detected by BMU (40) and/or based on other conditions. In addition or in the alternative, drugs may be delivered from PRU (70) based on direct commands from a physician/clinician/nurse/etc., and a safety shell may simply restrict the delivery of drugs to the patient to ensure that the patient is not inadvertently overmedicated by the physician/clinician/nurse/etc. In addition or in the alternative, a safety shell may provide instructions to the physician/clinician/nurse/etc. regarding drug delivery and/or regarding the condition of the patient, based on data from BMU (40) and/or based on other conditions. Various suitable hardware components and firmware configurations that may be used to provide a safety shell control logic in PRU (70) will be apparent to those of ordinary skill in the art in view of the teachings herein. In the present example, the ultimate goal of a safety shell is to keep the patient safe.

Some versions of system (10) may be dedicated to use in certain medical procedures (e.g., colonoscopy and/or Esophagogastroduodenoscopy (EGD) procedures, etc.). For instance, a PRU (70) may be dedicated to a particular type of procedure, such that the safety shell control algorithm is relatively consistent each time PRU (70) is used. Some such versions of system (10) may thus include a relatively static set of safety shell control algorithms. However, some other versions of system (10) may be configured for use in various types of different medical procedures. In some such versions, the control logic carried out through a safety shell may vary based on the type of medical procedure in which system (10) will be used. For instance, the control logic may monitor different patient physiological parameters through BMU (40), based on the type of medical procedure in which system (10) will be used. In addition or in the alternative, the control logic may be responsive to different thresholds or trends in patient physiological parameters as detected through BMU (40), based on the type of medical procedure in which system (10) will be used. In addition or in the alternative, PRU (70) may vary the type, amount, timing, and/or duration, etc. of drug delivery based on the type of medical procedure in which system (10) will be used.

In versions where the safety shell control algorithm is adaptive based on the type of medical procedure in which system (10) will be used, there are various ways in which PRU (70) may be informed of the type of medical procedure in which system (10) will be used. In some such versions, the determination may be automated. For instance, the type of drug cassette (86) selected by a user may vary based on the medical procedure, and drug cassette (86) may include a barcode that is scanned by a reader coupled with PRU (70). PRU (70) may then process the reading from the barcode to automatically select the appropriate safety shell control algorithm or sub-algorithm. As another merely illustrative variation, drug cassette (86) may include an RFID chip or similar feature, and PRU (70) may include a reader associated with a slot that receives drug cassette (86). PRU (70) may process a reading from the RFID chip to automatically select the appropriate safety shell control algorithm or sub-algorithm. It should also be understood that PRU (70) may be manually informed of the type of medical procedure in which system (10) will be used. For instance, a user may make a selection via touch screen assembly (42), via touch screen assembly (72), via a computer device that is coupled with system (10) via a network, and/or via some other user input feature. Various other suitable ways in which system (10) may be informed of the type of medical procedure in which system (10) will be used will be apparent to those of ordinary skill in the art in view of the teachings herein. Furthermore, it should be understood that the safety shell control algorithm may be adaptive based on the type of patient (e.g., patient's physical sensitivity and/or known responsiveness to drugs, etc.) involved in the medical procedure. System (10) may be informed of the type of patient manually (e.g., via touchscreens (42, 72), etc.), based on data from a network, based on data from BMU (40), and/or otherwise.

It should also be understood that an adaptive safety shell control algorithm may be constructed in a nodal network fashion, with each node being associated with a single function of system (10) within the algorithm. Each node has a unique set of discrete, defined logic. This logic then has a communication aspect that communicates with the other nodes. The nodes in concert create a singular cohesive logical system. This may provide the ability to selectively enable/disable each node as well as modify a singular node, limiting a change or adaptation (prior to procedure or on the fly as assessed by the system) to that node. In some versions, parameter logic statements and actions may be defined by individual events with abstract relationships that provide actions/triggers. If a new parameter is required, the introduction of a nodal parameter/link relationship may provide a modified logic (e.g., instead of providing a new if/then nested set of logic, etc.). It may also be possible for nodes to be removed. Furthermore, concepts of fuzzy logic and/or neural networks may be employed within a nodal network type of control algorithm, allowing the control algorithm to handle case based ambiguity such as the relationship between different patient physiological parameters. It should thus be understood that a nodal network type of logic structure may provide significant flexibility, facilitating accommodation of different medical procedures and patients.

As one merely illustrative example of how a safety shell control algorithm may adapt to a given medical procedure and/or patient, the duration of an initial drug dose or "loading dose" may be extended for a patient who demonstrates a relatively high physical sensitivity as compared to other patients. If system (10) detects that the patient has lost all responsiveness (e.g., has gone completely unconscious) during a loading dose, system (10) may adapt by adjusting the future administration of loading doses (e.g., increasing the duration beyond three minutes and reducing the quantity) and/or by adjusting the amount provided during a subsequent maintenance dose, etc. If a patient is very responsive after a loading dose, system (10) may also adapt by adjusting the future administration of loading doses (e.g., decreasing the duration below three minutes and increasing the quantity). As another merely illustrative example, system (10) may increase the delay between pro re nata (PRN) doses (e.g., to greater than ninety seconds) and/or decrease the size of the PRN dose if the patient desaturates or becomes non-responsive after a PRN. If the patient remains relatively responsive after a PRN, system (10) may decrease the delay between PRN doses (e.g., to less than ninety seconds) and/or increase the size of the PRN dose.

As a medical procedure continues in duration, the patient may accumulate drug in tissues beyond plasma and the nervous system. This accumulation may eventually re-release into the plasma after the drug delivery is decreased. Allowable maintenance rate increases, PRN dose size, etc. may thus be decreased over time, compensating for this accumulation. If the patient has many "false alarms" confirmed by the clinician via a user input of system (10), over a long procedure, system (10) may adapt and become less responsive to such an alarm. For instance, system (10) may provide thirty second delays between an alarm and an associated drug action, with a prompt asking the clinician (e.g., via touchscreen (42) and/or touchscreen (72)) if it is a false alarm. This may substantially prevent nuisance drug stoppage.

Several additional exemplary variations of patient care system (10) will be described in greater detail below, while other variations will be apparent to those of ordinary skill in the art in view of the teachings herein. It should also be understood that one or more parts and/or aspects of patient care system may be provided in accordance with the teachings of U.S. Pat. No. 6,745,764 and/or the teachings of U.S. Pat. No. 7,833,213, each of which is incorporated by reference herein.

II. Exemplary Open Architectural Framework

Figure 7:
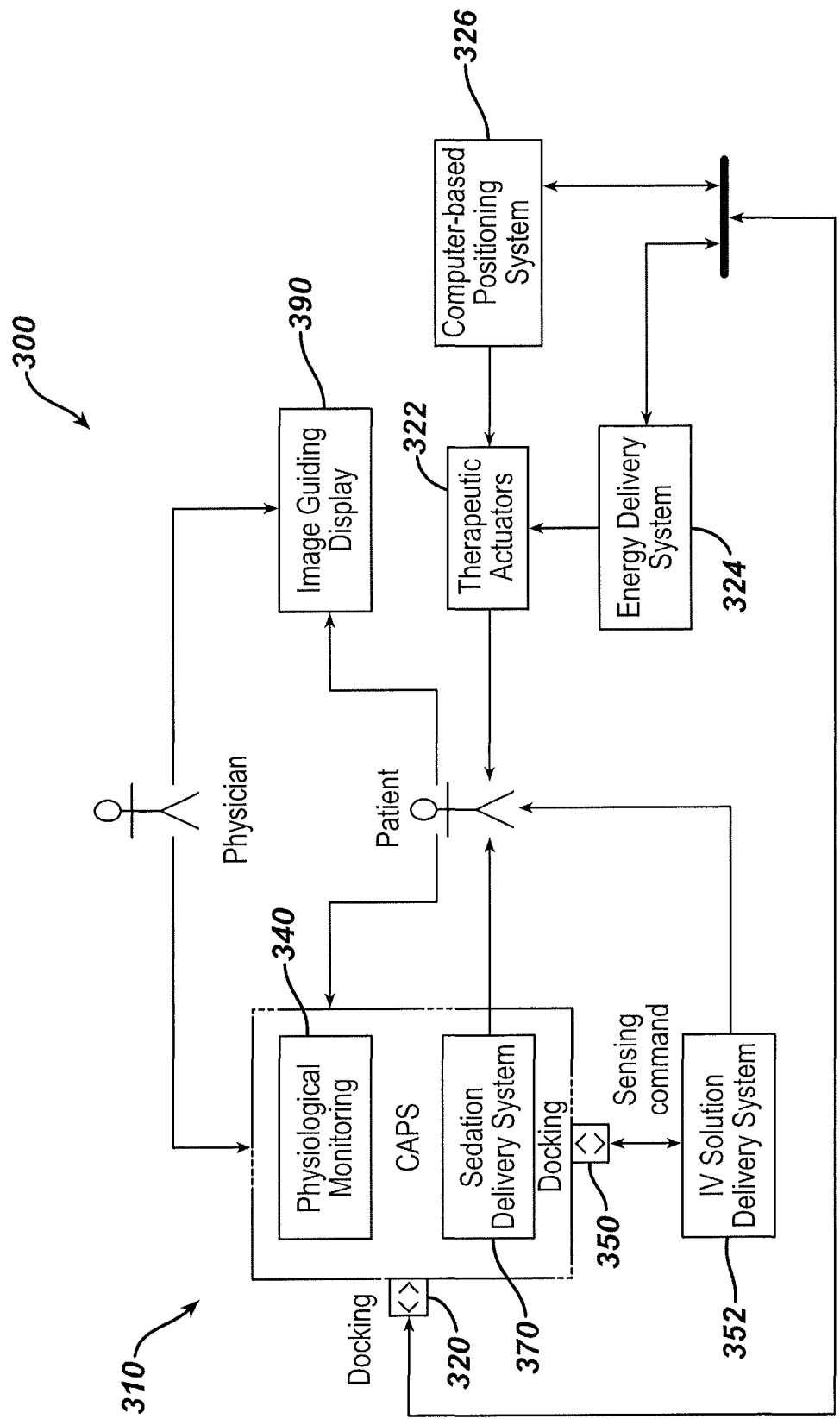
FIG. 7 depicts a schematic diagram of an exemplary patient monitoring and drug delivery system having an open architecture interfaced with additional devices.

Some versions of patient care system (10) are provided as a closed system. For instance, some such versions may simply consist of BMU (40) and PRU (70) coupled together and coupled with the patient. Some other versions of patient care system (10) may be provided as an open system, allowing various other devices and subsystems, etc. to interface with system (10). A merely illustrative example of such an open system (300) is shown in FIG. 7. System (300) of this example comprises a patient care system (310), which itself comprises a BMU (340), a PRU (370), an ancillary device dock (320), and an IV solution delivery system dock (350). In some versions of patient care system (310), BMU (340) and PRU (370) include the same components and functionality as BMU (40) and PRU (70) described above. System (300) of this example also includes a therapeutic instrument (322), an energy delivery system (324), and a positioning system (326) as ancillary devices that are coupled with patient care system (310) through dock (320). It should be understood, however, that various other types of devices could be coupled with patient care system (310) through dock (320), in addition to or in lieu of those ancillary devices described herein. For instance, an image guiding display (390) is shown as an ancillary device that is not coupled with patient care system (310), though it could be coupled with patient care system (310) in other versions. By way of example only, either or both of touchscreens (42, 72) could display images from an imaging system such as an ultrasound imaging system, etc.

In the present example, one of the ancillary devices comprises a therapeutic instrument (322) that may be coupled with dock (320). Therapeutic instrument (322) may include an RF ablation instrument, a HIFU instrument, a cryoablation instrument, or any other type of instrument operable to deliver therapy to a patient. Other suitable types of instruments that may be used as therapeutic instrument (322) will be apparent to those of ordinary skill in the art in view of the teachings herein. It should also be understood that therapeutic instrument (322) may be substituted or supplemented with various kinds of surgical instruments, which may also be coupled with dock (320). As will be described in greater detail below, patient care system (310) may provide data and/or commands to therapeutic instrument (322) via dock (320), such that operation of therapeutic instrument (322) may be affected (e.g., in real time) by data acquired from BMU (340), data input into PRU (370), etc. It should also be understood that therapeutic instrument (322) may provide data and/or commands to patient care system (310) via dock (320), such that operation of patient care system (310) may be affected (e.g., in real time) by feedback from therapeutic instrument (322), etc. Thus, it should be understood that patient care system (310) may be in uni-directional communication (in either direction) or in bi-directional communication with therapeutic instrument (322).

Therapeutic instrument (322) receives energy directly from energy delivery system (324) in the present example, though it should be understood that therapeutic instrument (322) may receive energy from patient care system (310) (e.g., regulated power delivery, etc.). Energy delivery system (324) may also receive data and/or commands, as well as power, from patient care system (310) via dock (320). Likewise, patient care system (310) may receive data and/or commands from energy delivery system (324).

Another ancillary device of system (300) is positioning system (326), which is operable to move therapeutic instrument (322) to control where therapeutic instrument (322) delivers therapy in a patient. As with therapeutic instrument (322) and energy delivery system (324), positioning system (326) may receive data and/or commands from patient care system (310) via dock (320). For instance, positioning system (326) may track patient responses to therapeutic instrument (322) in real time via BMU (340), and positioning system (326) may adjust the position of therapeutic instrument (322) in real time based on data from BMU (340). Of course, patient care system (310) may receive data and/or commands from therapeutic instrument (322). For instance, PRU (370) may adjust the delivery of drugs to the patient based on the location to which positioning system (326) has moved therapeutic instrument (322) and/or based on activation of therapeutic instrument (322), etc. PRU (370) may also adjust the delivery of drugs to the patient based on other data from therapeutic instrument (322). Other suitable ways in which patient care system (310) may interact with ancillary devices (322, 324, 326) will be apparent to those of ordinary skill in the art in view of the teachings herein. Similarly, other suitable types of ancillary devices that may be coupled with dock (320) will be apparent to those of ordinary skill in the art in view of the teachings herein.

In the present example, docks (320, 350) provide a hardware interface between patient care system (310) and ancillary devices. For instance, patient care system (310) may provide power to ancillary devices through docks (320, 350), such that patient care system (310) acts as a power hub. In some such versions, docks (320, 350) provide wired transmission of power through one or more plug and socket couplings and/or through any other suitable type of coupling. Alternatively, power may be communicated from patient care system (310) to one or more ancillary devices wirelessly, such as via an inductive coupling. It should also be understood that docks (320, 350) may provide communication of data and/or commands between patient care system (310) and ancillary devices. Again, such communication may be through one or more plug and socket couplings and/or through any other suitable type of coupling. As another merely illustrative example, data and/or commands may be communicated between patient care system (310) and ancillary devices wirelessly, such as through a conventional wireless RF communication protocol (e.g., Bluetooth, etc.), via infrared, or in any other suitable fashion. It should also be understood that such communication may be unidirectional or bi-directional. Furthermore, it should be understood that the presence of ancillary devices may be accounted for in a safety shell control algorithm of patient care system (310).

In versions where patient care system (310) receives data and/or commands from one or more ancillary devices coupled through dock (320), such ancillary devices may control which physiological parameters will be monitored by BMU (340) (and/or which physiological parameters PRU (370) will process from BMU (340)), which version of a safety shell control algorithm will be executed by PRU (370), the type/amount/duration/timing of drugs delivered by PRU (370), and/or some other aspect of how patient care system (310) operates. Similarly, in versions where one or more ancillary devices receive data and/or commands from patient care system (310), such data and/or commands may affect how the ancillary devices operate. For instance, one or more ancillary devices (e.g., electrosurgical device, etc.) may be at least temporarily disabled in instances where BMU (370) detects an alarming condition in the patient.

In some versions, patient care system (310) acts as a control hub, providing an equivalent to a computer operating system. Such an architecture may enable third parties to write programs that may be executed by patient care system (310), based on the third parties' unique implementation of patient care system (310) (e.g., for specific medical procedures) and/or based on the third parties' own ancillary devices that the third party wishes to have controlled in part by patient care system (310). In some versions of system (300), patient care system (310) provides one or more standardized interface specifications that must be met by ancillary devices coupling with dock (320) and/or IV solution delivery systems (352) coupling with dock (350). Such interface specifications may define the software/firmware interfaces that will be required in order for ancillary devices to be compatible with patient care system (310). In addition to software/firmware interfaces, the standardized interface specifications for patient care system (310) may define hardware interfaces (e.g., plug and socket configurations, etc.) that ancillary devices must comply with in order to physically couple with docks (320, 350). Of course, the software/firmware interface specification for dock (320) may differ from the software/firmware interface specification for dock (350). Similarly, the hardware interface specification for dock (320) may differ from the hardware interface specification for dock (350).

It should therefore be understood that patient care system (310) may enable manufacturers and other providers of ancillary devices to tailor their ancillary devices to be operable with patient care system (310). For instance, a third party developer of an electrosurgical device may develop an electrosurgical device that meets the software/firmware interface specifications as well as the hardware interface specifications in order to be compatible with patient care system (310). Furthermore, that same third party developer can develop control algorithms within their electrosurgical device that are responsive to data acquired through BMU (340) of patient care system (310) and/or other data from patient care system (310). Providing compatibility with patient care system (310) may thus increase functionality for ancillary devices (e.g., providing functionality that would not exist without real time data from BMU (40), etc.).

In addition or in the alternative to the above scenario where ancillary devices are tailored to be compatible with patient care system (310), system (300) may include one or more adapters that make a preexisting, off the shelf ancillary device compatible with patient system (310). For instance, such an adapter may include a hardware adapter that allows a power plug and/or data plug of a preexisting ancillary device to interface with a power socket and/or data socket of patient care system (310). In addition or in the alternative, an adapter may include a software/firmware interface adapter that essentially translates between protocols of patient care system (310) and protocols of a given ancillary device. It should be understood that software/firmware interface adapters may be added and/or updated (e.g., via a network, etc.) to accommodate a preexisting version of patient care system (310) to additional ancillary devices.

It should be understood from the foregoing that allowing ancillary devices to interface with patient care system (310) may make it easier for a user of system (300) to simultaneously monitor and control the various components of system (300). For instance, the user may be able to simply look at one display screen of patient care system (310), which may include information about ancillary devices, instead of having to look at several display screens on various ancillary devices. In addition, in versions where patient care system (310) is operable to at least partially control ancillary devices, based on data acquired through BMU (340) or otherwise, such automated control may reduce the need for the user to make manual adjustments to several different ancillary devices individually during a medical procedure. In other words, in scenarios where the user might otherwise have to interface with several different isolated systems, each with their own operation interface an each being unable to communicate with the other, it may significantly increase the convenience to the user to have all of the functionality tied together in a single comprehensive system (300) with a single user interface.

III. Exemplary Centralization

A. Exemplary Docking Station for BMUs

Figure 8:
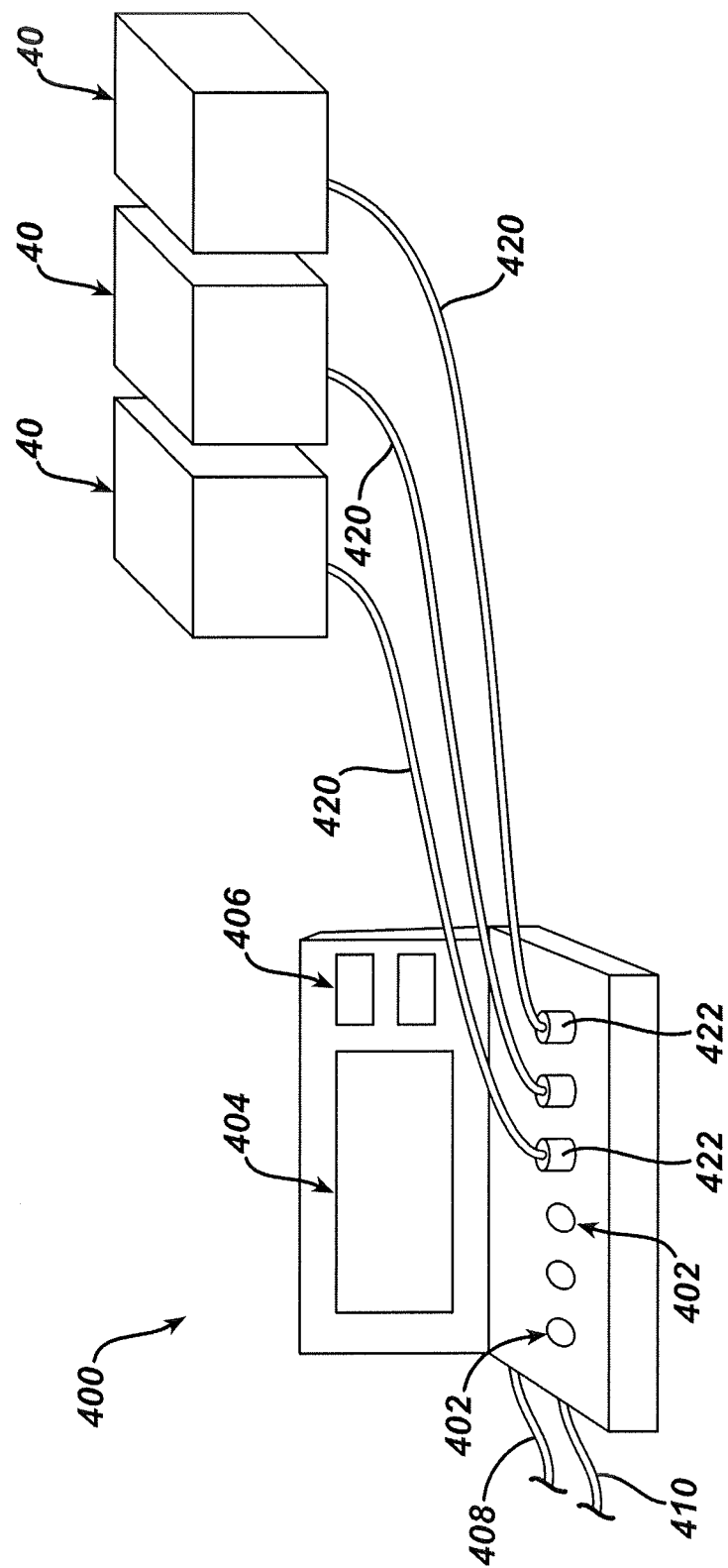
FIG. 8 depicts a perspective view of an exemplary docking station for patient monitoring units.
Figure 9:
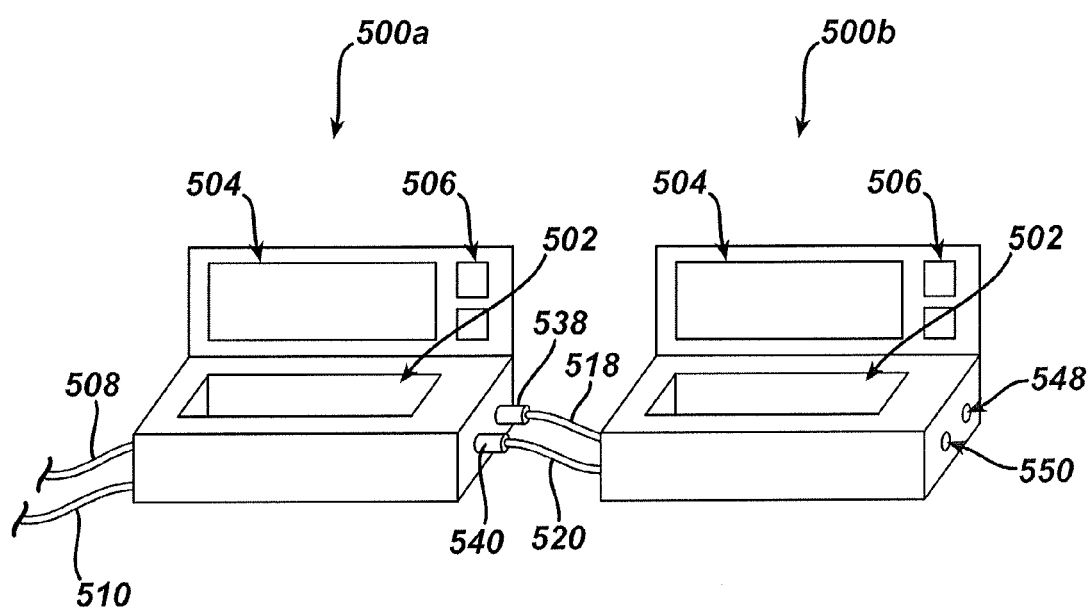
FIG. 9 depicts a perspective view of another exemplary docking station for patient monitoring units.
Figure 10:
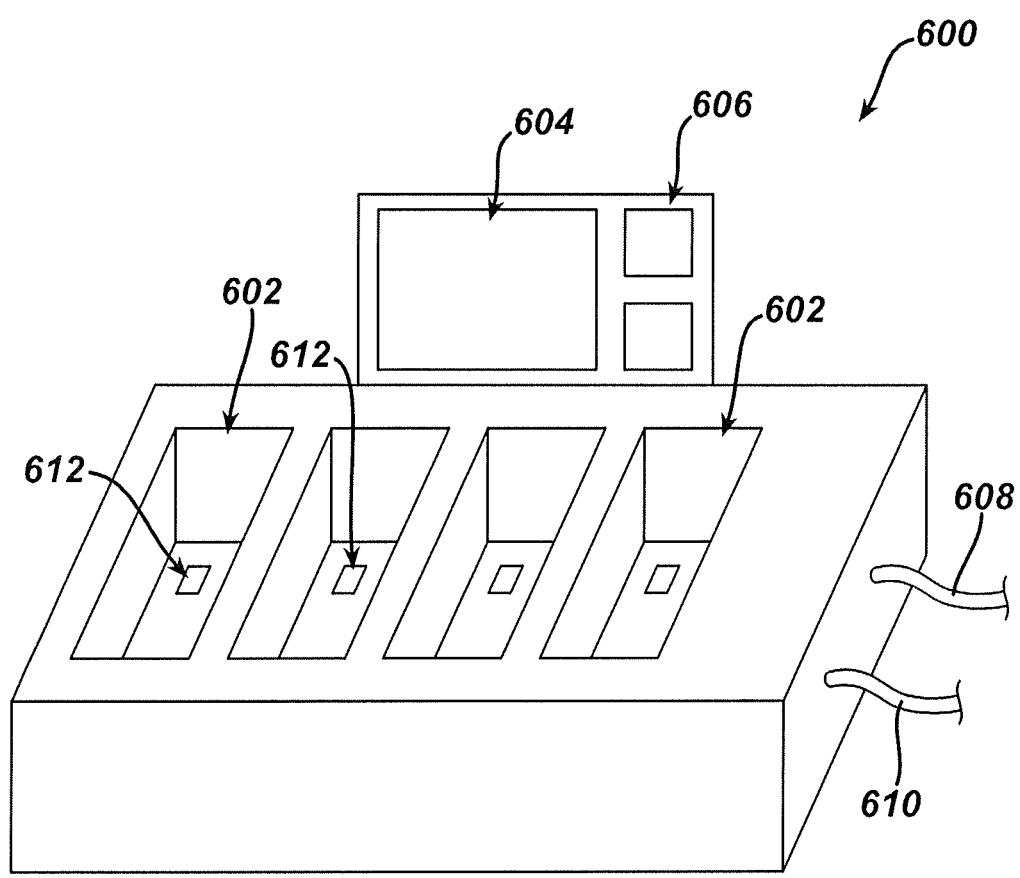
FIG. 10 depicts a perspective view of another exemplary docking station for patient monitoring units.

FIGS. 8-10 show exemplary docking stations (400, 500, 600) that may be used with some versions of BMU (40). In particular, as will be described in greater detail below, docking stations (400, 500, 600) are operable to couple with BMUs (40) to provide power and/or data communication with several BMUs (40) simultaneously. For instance, each type of docking station (400, 500, 600) may be used to recharge batteries (44) of BMUs (40) and to calibrate batteries (44) and/or other hardware of BMUs (40). It should be understood that such calibration may be automatic, occurring as soon as BMUs (40) are coupled with docking stations (400, 500, 600), with docking stations (400, 500, 600) automatically determining the calibration needs of BMUs (40). Similarly, docking stations (400, 500, 600) may perform diagnostics on BMUs (40) upon coupling of BMUs (40) with docking stations (400, 500, 600). In some versions, each docking station (400, 500, 600) provides smart charging of batteries (44), such as by monitoring battery status, battery health, and/or battery usage information and adjusting a charge strategy accordingly in order to optimize the charge and the life of battery (44). If BMUs (40) are coupled with docking stations (400, 500, 600) at the end of each day, such coupling may prevent batteries (44) from deep discharging.

While docking stations (400, 500, 600) are described below as coupling with BMUs (40), it should be understood that some other versions of docking stations (400, 500, 600) may simply couple directly with batteries (44). A user could thus simply decouple battery (44) from BMU (40) and couple battery (44) with docking station (400, 500, 600) in order to recharge battery (44). Such versions of docking stations (400, 500, 600) may couple with batteries (44) in various ways similar to those described below with respect to coupling of docking stations (400, 500, 600) with BMUs (40). It should also be understood that some versions of docking stations (400, 500, 600) may lack battery charging capabilities. For instance, sets of pre-charged batteries may be kept and recharged separately and may be used to replace used batteries (44) each day or otherwise as needed. In some such versions, docking stations (400, 500, 600) are simply used to communicate data from and/or to BMUs (40), as described herein or otherwise. In addition, while docking stations (400, 500, 600) are described below as coupling with several BMUs (40) simultaneously, some versions or uses of docking stations (400, 500, 600) may provide or include only docking a single BMU (40) with docking station (400, 500, 600). Thus, it should be understood that any teaching herein of several ports being included as part of a docking station (400, 500, 600) may be modified to just a single port.

Docking stations (400, 500, 600) may also receive data from BMUs (40). Such data may include data relating to use of BMUs (40) and/or PRUs (70), which may in turn be used for billing purposes, for purposes of determining when BMUs (40) and/or PRUs (70) will need to be serviced or replaced, for purposes of determining whether disposable components associated with BMUs (40) and/or PRUs (70) should be disposed of or reconditioned, for purposes of detecting misuse of BMUs (40) and/or PRUs (70), and/or for other purposes. In addition or in the alternative, docking stations (400, 500, 600) may also receive data from BMUs (40) relating to patients. For instance, if BMUs (40) are coupled with docking stations (400, 500, 600) at the end of each day, docking stations (400, 500, 600) may receive data from BMUs (40) relating to patients who were coupled with BMUs (40) that day.

As described in greater detail below, docking stations (400, 500, 600) may also be coupled with a remote server or other type of computer system via a network, such that docking stations (400, 500, 600) may transmit at least some data from BMUs (40) to the remote server or other type of computer system via the network. By way of example only, docking stations (400, 500, 600) may transmit data relating to use of BMUs (40) and/or PRUs (70), use of disposable components associated with BMUs (40) and/or PRUs (70), etc., to a remote location. As another merely illustrative example, patient information collected from BMUs (40) may be transmitted from docking station (400, 500, 600) to a physician's electronic medical records system through a local data transfer (e.g., via a USB connection, memory card transfer, LAN connection, etc.) or through a network (e.g., to a remote server, etc.). Furthermore, a physician (or computer system) at a remote location may make a diagnosis (and/or perform some other kind of analysis) of a patient based on information from a BMU (40) that is transmitted to the remote location via docking station (400, 500, 600) and the network. When a plurality of BMUs (40) are coupled with docking stations (400, 500, 600), docking stations (400, 500, 600) may receive data from BMUs (40) individually (e.g., in serial fashion, etc.), simultaneously, or in any other suitable fashion.

In addition to or as an alternative to docking stations (400, 500, 600) receiving data from BMUs (40), BMUs (40) may receive data from docking stations (400, 500, 600). For instance, docking stations (400, 500, 600) may transmit software and/or firmware upgrades to several BMUs (40) simultaneously. By way of example only, docking stations (400, 500, 600) may transmit safety shell control algorithms to BMUs (40). BMUs (40) may in turn relay at least part of the data received from docking stations (400, 500, 600) to PRUs (70) when BMUs (40) are subsequently coupled with PRUs (70). As another merely illustrative example, docking stations (400, 500, 600) may be used to provide a configuration utility when a plurality of BMUs (40) are being used for the first time in a particular facility. In other words, a user may configure several BMUs (40) simultaneously by performing such configuration through docking stations (400, 500, 600).

As yet another merely illustrative example, docking stations (400, 500, 600) may allow data to be passed from one BMU (40) to another BMU (40). One implementation of this may be for docking stations (400, 500, 600) to provide data synchronization across a plurality of BMUs (40). For instance, some versions of drug cassette (86) include an RFID chip, barcode, or other identifier. Such an identifier may be used to help identify which drug cassettes (86) have been used with patients, and this usage data may be stored in a BMU (40) that is coupled with a PRU (70) having the used drug cassette (86). When BMUs (40) are later coupled with a docking station (400, 500, 600), this drug cassette (86) usage information may be shared among the BMUs (40) via docking station (400, 500, 600). All BMUs (40) in the group may thus have a more complete listing of used drug cassettes (86) than they might otherwise have. Therefore, when a BMU (40) is used again later, it may have a better capability of recognizing a used drug cassette (86) and may respond in various ways when it is coupled with a PRU (70) that has a previously used drug cassette (86). For instance, BMU (40) may provide an alert to the user via BMU (40) and/or via PRU (70) indicating that the drug cassette (86) has been previously used and should be replaced. In addition or in the alternative, BMU (40) may render BMU (40) and/or PRU at least partially inoperable when BMU (40) detects that the PRU (70) is being used with a previously used drug cassette (86).

It should also be understood that a remote server or other type of computer system may transmit data (e.g., software/firmware updates, etc.) to docking stations (400, 500, 600) via a network. Such data may be configured for use solely by docking stations (400, 500, 600); or for further transmission to BMUs (40) via docking stations (400, 500, 600). In some instances, a remote server or other type of computer system may transmit updates for PRUs (70) to docking stations (400, 500, 600) via a network. Such updates may be first transmitted from docking station (400, 500, 600) to BMU (40); and then from BMU (40) to PRU (70) (e.g., after BMU (40) is de-coupled from docking station (400, 500, 600) and then coupled with PRU (70)).

In some versions, docking station (400, 500, 600) receives updates for docking station (400, 500, 600), BMU (40), and/or PRU (70) as soon as those updates are available, regardless of whether BMU (40) is coupled with docking station (400, 500, 600). Docking station (400, 500, 600) then transmits updates to BMU (40) as needed when BMU (40) is coupled with docking station (400, 500, 600). It should be understood that the updates may be pushed to or pulled by docking station (400, 500, 600) from a remote system in such versions. In some other versions, docking station (400, 500, 600) queries a remote server or computer system for updates after a BMU (40) has been coupled with docking station (400, 500, 600), after docking station (400, 500, 600) receives a specific command from a user, and/or under some other condition(s). Then docking station (400, 500, 600) relays those updates to BMU (40) right after docking station (400, 500, 600) receives the updates. Various other suitable update scenarios and implementations will be apparent to those of ordinary skill in the art in view of the teachings herein.

In some versions, docking stations (400, 500, 600) also include an integral printer (not shown). Such a printer may be operable to print information relating to docking stations (400, 500, 600), information relating to data gathered from BMUs (40) coupled with docking stations (400, 500, 600), and/or various other kinds of information. The following will describe each exemplary version of docking station (400, 500, 600) in greater detail, though it should be understood that these versions are merely examples only. Various other suitable forms that docking stations (400, 500, 600) may take will be apparent to those of ordinary skill in the art in view of the teachings herein.

1. Exemplary Docking Station with BMU Cable Ports

FIG. 8 shows docking station (400) coupled with three BMUs (40) via respective cables (420). Docking station (400) of this example includes a plurality of sockets (402) that are configured to receive corresponding plugs (422) of cables (420). Sockets (402) and plugs (422) are configured to provide communication of power from docking station (400) to BMUs (40) and/or to provide communication of data between docking station (400) and BMUs (40), as described above. In some versions, cables (420) are the same as cables (20) described above. For instance, cable (420) may be configured to couple with PRU (70) as described above, and may be simply unplugged from PRU (70) and be plugged into a selected socket (402) of docking station (400). In some other versions, cable (420) is separate from cable (20). For instance, cable (420) may be a dedicated docking cable, may be a USB cable, or may have any other suitable configuration. It should also be understood that docking station (400) may transmit power and/or data to BMU (40) wirelessly. For instance, docking station (400) may transmit both power (e.g., for recharging battery (44), etc.) and data (e.g., to synchronize BMUs (40), to provide updates BMUs (40), etc.) via an inductive coupling. As another merely illustrative variation, docking station (400) may provide communication of power to BMU (40) via cable (420); and provide communication of data to BMU (40) wirelessly, or vice versa. Various other suitable ways in which power and/or data may be communicated will be apparent to those of ordinary skill in the art in view of the teachings herein.

Docking station (400) of this example also includes a display screen (404) and a user input feature (406). Display screen (404) is operable to display information about BMUs (40) that are coupled with docking station (400). By way of example only, display screen (404) may comprise an LCD screen capable of rendering graphics, a plurality of simple LEDs (e.g., one or more LEDs to show charging status, one or more LEDs to show docking station (400) being powered on, one or more LEDs to show errors, etc.), and/or any other suitable type of display. In some versions, display screen (404) simply shows which sockets (402) have cables (420) coupled with them. In addition or in the alternative, display screen (404) may show the charge status of batteries (44) of BMUs (40) that are coupled with docking station (400). In addition or in the alternative, display screen (404) may show other information communicated from BMUs (40) (e.g., information relating to use of BMU (40), information relating to a patient with whom BMU (40) was used, etc.). Other suitable types of information that may be provided through display screen (404), as well as various suitable forms that display screen (404) may take, will be apparent to those of ordinary skill in the art in view of the teachings herein. Of course, as with other components described herein, display screen (404) is merely optional. It should also be understood that display screen (404) may be substituted or supplemented with a speaker and/or some other audio output.

Regardless of whether display screen (404) is included, it should also be understood that screen (42) of BMU (40) may also provide information when BMU (40) is coupled with docking station (400). For instance, the coupling of plug (422) with socket (402) may cause screen (42) of BMU (40) to change modes and start displaying the charge status of battery (44) for that BMU (40). Screen (42) may also provide information regarding an update received from docking station (400) and/or other information associated with one or more docking processes. Other types of information that may be shown on screen (42) while BMU (40) is coupled with docking station (400) will be apparent to those of ordinary skill in the art in view of the teachings herein. It should also be understood that screen (42) may be substituted or supplemented with a speaker and/or some other audio output.

User input feature (406) may include a touch screen, input keys, and/or any other suitable type of feature(s) operable to receive user input. By way of example only, user input feature (406) may be manipulated by a user to retrieve updates from a remote device, to transmit updates to BMUs (40), to query BMUs (40) for information, to sort through information from BMUs (40), to change display modes on screen (42) and/or screen (404), and/or for any other functions. It should also be understood that display screen (404) and user input feature (406) may be consolidated (e.g., in a touch screen, etc.). Various suitable ways in which one or more user input features (406) may be provided and used will be apparent to those of ordinary skill in the art in view of the teachings herein. It should also be understood that, as with various other components referred to herein, user input feature (406) may simply be omitted, if desired.

Docking station (400) also includes a power cable (408) and a data cable (410). In the present example, power cable (408) and data cable (410) are separate cables, with power cable (408) providing power to docking station (400) and data cable (410) providing data communication between docking station (400) and a network. In some other versions, data and power communication are consolidated in a single cable (e.g., using powerline communication technology such as BPL adapters, etc.). Data cable (410) may comprise an Ethernet cable, a USB cable, a RS232 cable, a RS485 cable, and/or any other suitable type of cable that is operable to communicate data. It should also be understood that docking station (400) may include wireless communication capabilities, such that data cable (410) may be omitted if desired. Furthermore, docking station (400) may include a memory card interface, a USB port, and/or other type of data hardware interface, in addition to or in lieu of including a data cable (410) or wireless adapter. In some settings, these types of interfaces may be used to transmit data to docking station (400) and/or to transmit data from docking station (400), such as between a computer network and/or a laptop computer or other portable electronic device and docking station (400). This may be desirable in some instances where an Ethernet network connection is difficult to reach or it would be undesirable to have an Ethernet cable in the room; and/or instances where there may be problems with wireless communications standards.

In some settings, docking station (400) is secured to an IV pole, providing substantially ready mobility for docking station (400). In some other settings, docking station (400) is mounted to a wall, in a cabinet, or in any other suitable type of location. It should also be understood that some versions of docking station (400) may be mounted or otherwise positioned at a height that is roughly the same as the height of a BMU (40) that is mounted to an IV pole or other structure. Such positioning may facilitate coupling of BMUs (40) with docking station (400). Of course, docking station (400) may be positioned at any suitable location as desired.

2. Exemplary Chain of BMU Docking Stations

FIG. 9 shows a pair of docking stations (500) coupled together, though it will be understood that numerous additional docking stations (500) may also be coupled in a chain with docking stations (500). While docking stations (500) are numbered as "500a" and "500b" in FIG. 9, they will both be referred to herein collectively by reference number "500" when describing features common to both docking stations (500) in the present example. However, the below description will also include some examples where docking station (500a) is configured differently from docking station (500b). Each docking station (500) of the present example includes a docking recess (502) that is configured to receive a BMU (40). Each docking recess (502) includes a port (not shown) such as one or more contacts, an inductive coil, and/or other feature(s) configured to provide communication of power from docking station (500) to BMU (40) and/or to provide communication of data between docking station (500) and BMU (40), as described above. Such a port may be configured to provide a power/data coupling between docking station (500) and BMU (40) as soon as BMU (40) is fully seated in docking recess (502).

Docking station (500) of this example also includes a display screen (504) and a user input feature (506). Display screen (504) is operable to display information about BMU (40) that is coupled with docking station (400). By way of example only, display screen (504) may comprise an LCD screen capable of rendering graphics, a plurality of simple LEDs (e.g., one or more LEDs to show charging status, one or more LEDs to show docking station (500) being powered on, one or more LEDs to show errors, etc.), and/or any other suitable type of display. In some versions, display screen (504) may show the charge status of batteries (44) of BMU (40) that is coupled with docking station (500). In addition or in the alternative, display screen (504) may show other information communicated from BMU (40) (e.g., information relating to use of BMU (40), information relating to a patient with whom BMU (40) was used, etc.). Other suitable types of information that may be provided through display screen (504), as well as various suitable forms that display screen (504) may take, will be apparent to those of ordinary skill in the art in view of the teachings herein. Of course, as with other components described herein, display screen (504) is merely optional. It should also be understood that display screen (504) may be substituted or supplemented with a speaker and/or some other audio output.

Regardless of whether display screen (504) is included, it should also be understood that screen (42) of BMU (40) may also provide information when BMU (40) is coupled with docking station (500). For instance, the insertion of BMU (40) in docking recess (502) may cause screen (42) of BMU (40) to change modes and start displaying the charge status of battery (44) for that BMU (40). Screen (42) may also provide information regarding an update received from docking station (500) and/or other information associated with one or more docking processes. Other types of information that may be shown on screen (42) while BMU (40) is coupled with docking station (500) will be apparent to those of ordinary skill in the art in view of the teachings herein. It should also be understood that screen (42) may be substituted or supplemented with a speaker and/or some other audio output.

User input feature (506) may include a touch screen, input keys, and/or any other suitable type of feature(s) operable to receive user input. By way of example only, user input feature (506) may be manipulated by a user to retrieve updates from a remote device, to transmit updates to BMU (40), to query BMU (40) for information, to sort through information from BMU (40), to change display modes on screen (42) and/or screen (504), and/or for any other functions. It should also be understood that display screen (504) and user input feature (506) may be consolidated (e.g., in a touch screen, etc.). Various suitable ways in which one or more user input features (506) may be provided and used will be apparent to those of ordinary skill in the art in view of the teachings herein. It should also be understood that, as with various other components referred to herein, user input feature (506) may simply be omitted, if desired.

Docking station (500a) includes a power cable (508) and a data cable (510). In the present example, power cable (508) and data cable (510) are separate cables, with power cable (508) providing power to docking station (500a) and data cable (510) providing data communication between docking station (500a) and a network. In some other versions, data and power communication are consolidated in a single cable (e.g., using powerline communication technology such as BPL adapters, etc.). Data cable (510) may comprise an Ethernet cable, a USB cable, and/or any other suitable type of cable that is operable to communicate data. It should also be understood that docking station (500a) may include wireless communication capabilities, such that data cable (510) may be omitted if desired. Furthermore, docking station (500a) may include a memory card interface, a USB port, and/or other type of data hardware interface, in addition to or in lieu of including a data cable (510) or wireless adapter. In some settings, these types of interfaces may be used to transmit data to docking station (500a) and/or to transmit data from docking station (500a), such as between a computer network and/or a laptop computer or other portable electronic device and docking station (500a).

Docking station (500b) also includes a power cable (518) and a data cable (520). Power cable (518) includes a plug (538) received by a socket in docking station (500a), such that power is communicated from docking station (500a) to docking station (500b) via cable (518). Docking station (500b) also includes a socket (548), allowing another docking station (500) to be coupled thereto via cable, for further communication of power. It should be understood that several docking stations (500) may be coupled in this fashion, allowing power to be transmitted along all such docking stations (500) in the chain via cables or otherwise. Similarly, data cable (520) includes a plug (540) received by a socket in docking station (500a), such that data is communicated between docking station (500a) and docking station (500b) via cable (520). Docking station (500b) also includes a socket (550), allowing another docking station (500) to be coupled thereto via cable, for further communication of data. It should be understood that several docking stations (500) may be coupled in this fashion, allowing data to be transmitted along all such docking stations (500) in the chain via cables or otherwise.

In the present example, power cable (508) and data cable (510) are separate cables, with power cable (508) providing power to docking station (500a) and data cable (510) providing data communication between docking station (500a) and a network. In some other versions, data and power communication are consolidated in a single cable (e.g., using powerline communication technology such as BPL adapters, etc.). Data cable (510) may comprise an Ethernet cable, a USB cable, a RS232 cable, a RS485 cable, and/or any other suitable type of cable that is operable to communicate data. It should also be understood that docking station (500a) may include wireless communication capabilities, such that data cable (510) may be omitted if desired. Furthermore, docking station (500a) may include a memory card interface, a USB port, and/or other type of data hardware interface, in addition to or in lieu of including a data cable (510) or wireless adapter. In some settings, these types of interfaces may be used to transmit data to docking station (500a) and/or to transmit data from docking station (500a), such as between a laptop computer or other portable electronic device and docking station (500a). This may be desirable in some instances where an Ethernet network connection is difficult to reach or it would be undesirable to have an Ethernet cable in the room; and/or instances where there may be problems with wireless communications standards. Likewise, either or both of cables (518, 520) may be subject to the same variations described above with respect to cables (508, 510).

In some versions, docking station (500a) serves as a main docking station, while docking station (500b) (and other docking stations (500) that are coupled thereto) serve as passive stations. For instance, in some versions docking station (500a) is the only docking station (500) in the chain that includes display screen (504) and/or user input feature (506). In addition or in the alternative, in some versions docking station (500a) includes the main charging circuitry, memory, and/or additional processing circuitry/hardware, while docking station (500b) and others in the chain simply act as relays to docking station (500a). In versions where docking station (500a) serves as a main docking station, and regardless of whether docking station (500b) or other docking stations include display screen (504), the display screen (504) of docking station (500a) may display information about docking station (500b) or other docking stations and/or information about BMUs (40) that are coupled with docking station (500b) or other docking stations. Similarly, in versions where docking station (500a) serves as a main docking station, and regardless of whether docking station (500b) or other docking stations include user input feature (506), the user input feature (506) of docking station (500a) may be used to control docking station (500b) or other docking stations and/or to control BMUs (40) that are coupled with docking station (500b) or other docking stations. Various other suitable ways in which components and functionality may be allocated between docking station (500a) and other docking stations such as docking station (500b) will be apparent to those of ordinary skill in the art in view of the teachings herein.

3. Exemplary Docking Station with BMU Docking Recesses

Figure 11:
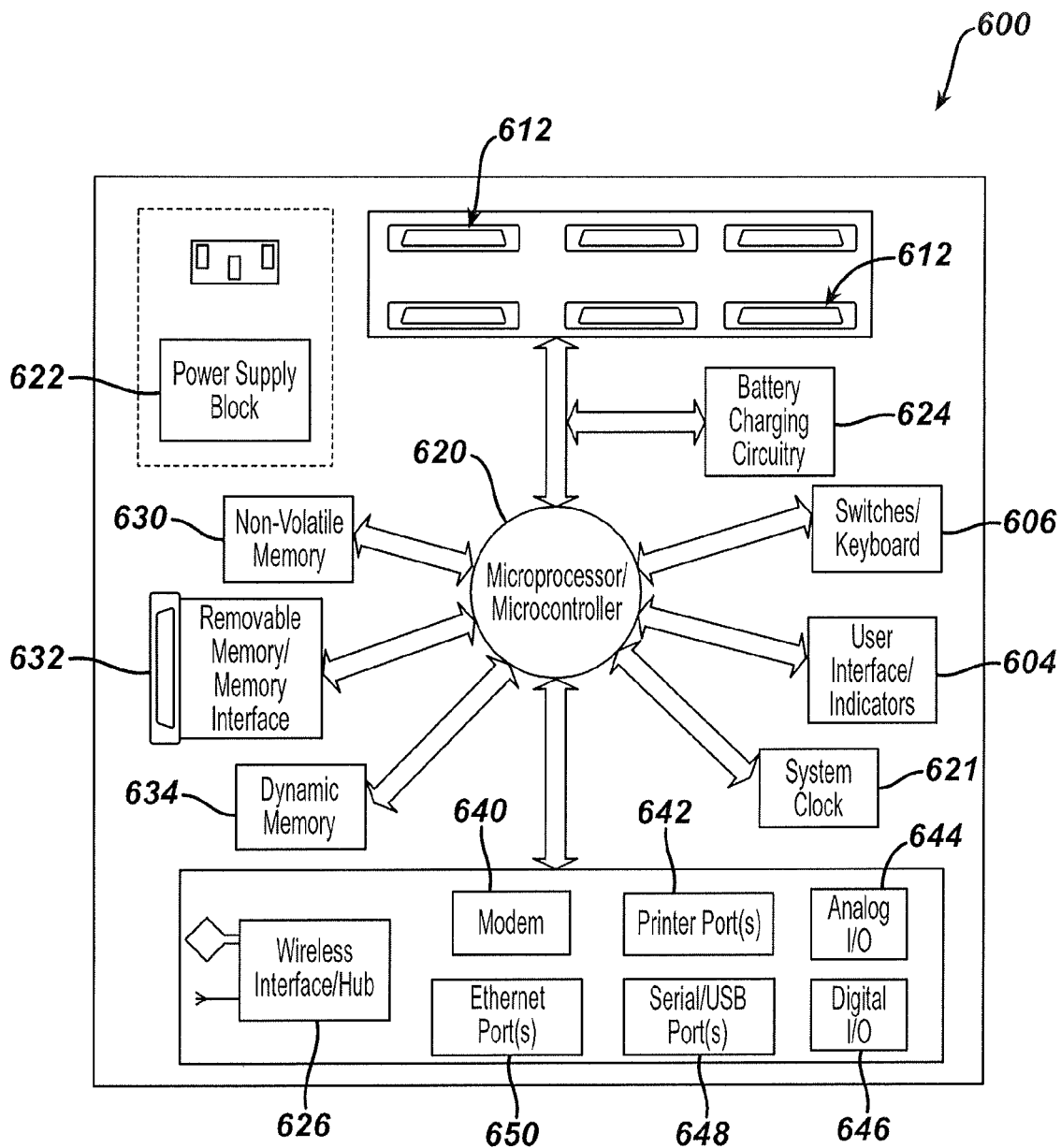
FIG. 11 depicts a block schematic diagram of the docking station of FIG. 10.

FIGS. 10-11 show docking station (600) having a plurality of docking recesses (602) that are configured to receive BMUs (40). Each docking recess (602) includes a port (612) configured to provide communication of power from docking station (600) to BMU (40) and/or to provide communication of data between docking station (600) and BMU (40), as described above. Each port (612) may be configured to provide a power/data coupling between docking station (600) and BMU (40) as soon as BMU (40) is fully seated in docking recess (602). By way of example only, port (612) may comprise one or more contacts, an inductive coil, and/or other feature(s). Each port (612) is in communication with a processor (620) within docking station (600). A system clock (621) is also in communication with processor (620).

Docking station (600) of this example also includes a display screen (604) and a user input feature (606), each of which are also in communication with processor (620). Display screen (604) is operable to display information about BMUs (40) that are coupled with docking station (600). By way of example only, display screen (604) may comprise an LCD screen capable of rendering graphics, a plurality of simple LEDs (e.g., one or more LEDs to show charging status, one or more LEDs to show docking station (600) being powered on, one or more LEDs to show errors, etc.), and/or any other suitable type of display. In some versions, display screen (604) simply shows which docking recesses (602) have BMUs (40) inserted in them. In addition or in the alternative, display screen (604) may show the charge status of batteries (44) of BMUs (40) that are coupled with docking station (600). In addition or in the alternative, display screen (604) may show other information communicated from BMUs (40) (e.g., information relating to use of BMU (40), information relating to a patient with whom BMU (40) was used, etc.). Other suitable types of information that may be provided through display screen (604), as well as various suitable forms that display screen (604) may take, will be apparent to those of ordinary skill in the art in view of the teachings herein. Of course, as with other components described herein, display screen (604) is merely optional. It should also be understood that display screen (604) may be substituted or supplemented with a speaker and/or some other audio output.

Regardless of whether display screen (604) is included, it should also be understood that screen (42) of BMU (40) may also provide information when BMU (40) is coupled with docking station (600). For instance, the insertion of BMU (40) in docking recess (602) may cause screen (42) of BMU (40) to change modes and start displaying the charge status of battery (44) for that BMU (40). Screen (42) may also provide information regarding an update received from docking station (600) and/or other information associated with one or more docking processes. Other types of information that may be shown on screen (42) while BMU (40) is coupled with docking station (600) will be apparent to those of ordinary skill in the art in view of the teachings herein. It should also be understood that screen (42) may be substituted or supplemented with a speaker and/or some other audio output.

User input feature (606) may include a touch screen, input keys, and/or any other suitable type of feature(s) operable to receive user input. By way of example only, user input feature (606) may be manipulated by a user to retrieve updates from a remote device, to transmit updates to BMU (40), to query BMU (40) for information, to sort through information from BMU (40), to change display modes on screen (42) and/or screen (604), and/or for any other functions. It should also be understood that display screen (604) and user input feature (606) may be consolidated (e.g., in a touch screen, etc.). Various suitable ways in which one or more user input features (606) may be provided and used will be apparent to those of ordinary skill in the art in view of the teachings herein. It should also be understood that, as with various other components referred to herein, user input feature (606) may simply be omitted, if desired.

Docking station (600) also includes a power cable (608) and a data cable (610). Power cable (608) is in communication with a power supply feature (622) in docking station (600). Power supply feature (622) provides power to battery charging circuitry (624) and other components of docking station (600). Battery charging circuitry (624) is operable to charge batteries (44) of BMUs (40) that are received in docking recesses (602) as described above. In the present example, power cable (608) and data cable (610) are separate cables, with power cable (608) providing power to docking station (600) and data cable (610) providing data communication between docking station (600) and a network. In some other versions, data and power communication are consolidated in a single cable (e.g., using powerline communication technology such as BPL adapters, etc.). Data cable (610) may comprise an Ethernet cable, a USB cable, and/or any other suitable type of cable that is operable to communicate data. It should also be understood that docking station (600) may include wireless communication capabilities, such that data cable (610) may be omitted if desired. For instance, FIG. 11 shows docking station (600) including a wireless interface/hub (624).

It should be understood that processor (620) may communicate with various kinds of memory. For instance, as shown in FIG. 11, docking station (600) of the present example includes an internal non-volatile memory (630), an internal volatile memory (632), and a memory card interface (634), all of which are in communication with processor (620). As with other components referred to herein, each of these memory components may be substituted, supplemented, or even omitted, as desired. FIG. 11 also shows various types of ports that may optionally be included in docking station (600), including a modem (640), a printer port (642), an analog input/output port (644), a digital input/output port (646), a USB port (648), and an Ethernet port (650), all of which are shown as being in communication with processor (620). In some settings, these types of interfaces may be used to transmit data to docking station (600) and/or to transmit data from docking station (600), such as between a laptop computer, a computer network, or other electronic device and docking station (600). Other suitable types of ports that may be included with docking station (600) will be apparent to those of ordinary skill in the art in view of the teachings herein. By way of example only, a wireless port, an RS232 port, an RS485 port, and/or an I2C port may be provided in addition to or in lieu of any of the ports listed above. Of course, docking station (600) need not have a plurality of ports, and may simply omit most if not all of the ports listed above, etc. Other suitable components, features, configurations, and operabilities that may be incorporated into docking station (600) will be apparent to those of ordinary skill in the art in view of the teachings herein. It should also be understood that various components that are shown in FIG. 11 may be readily incorporated into docking stations (400, 500), even though these components are shown in the context of docking station (600).

4. Exemplary Processes Carried Out through Docking Stations

Figure 12A:
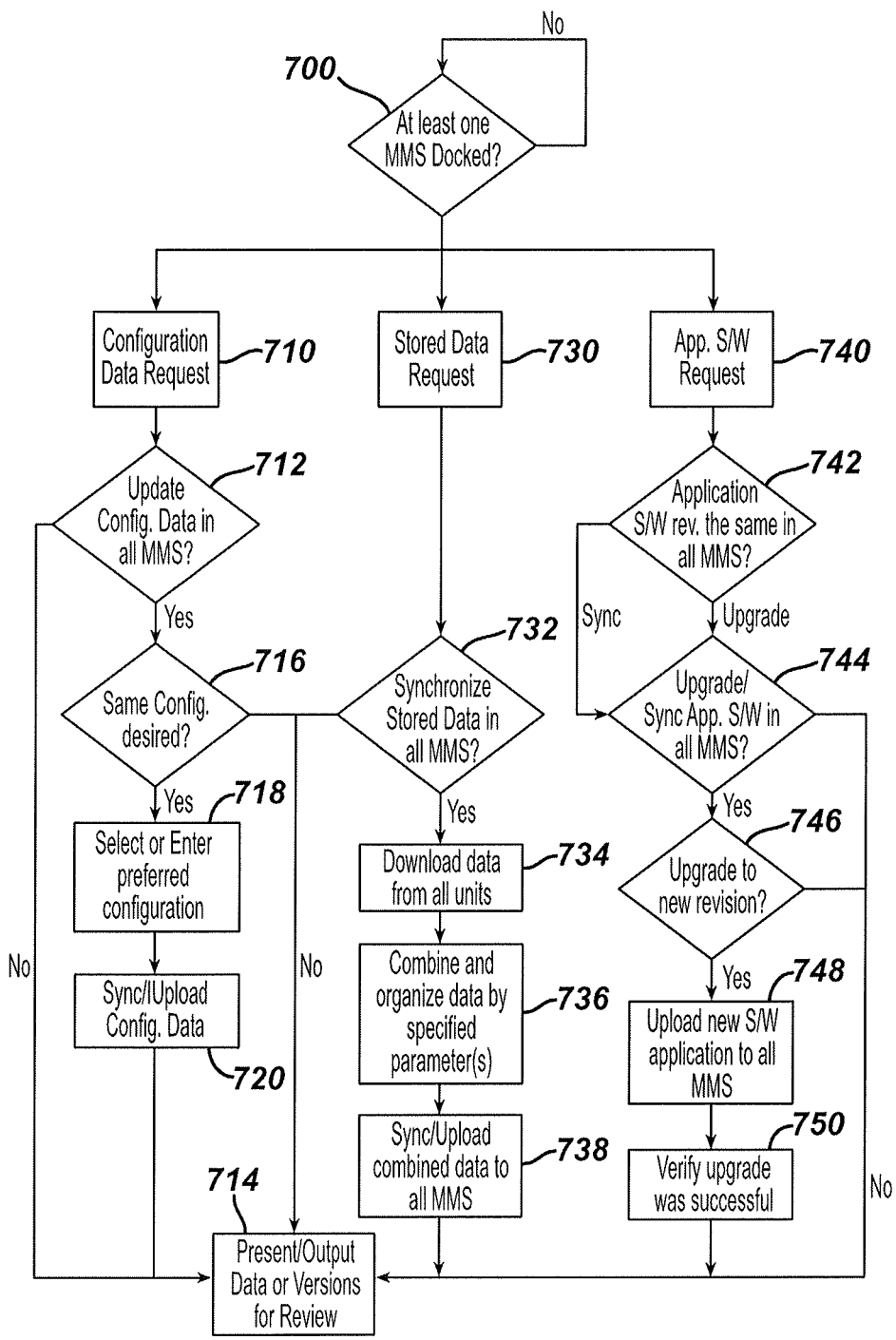
FIG. 12A depicts a flow diagram of an exemplary process that may be carried out using the docking stations of FIGS. 9-11.
Figure 12B:
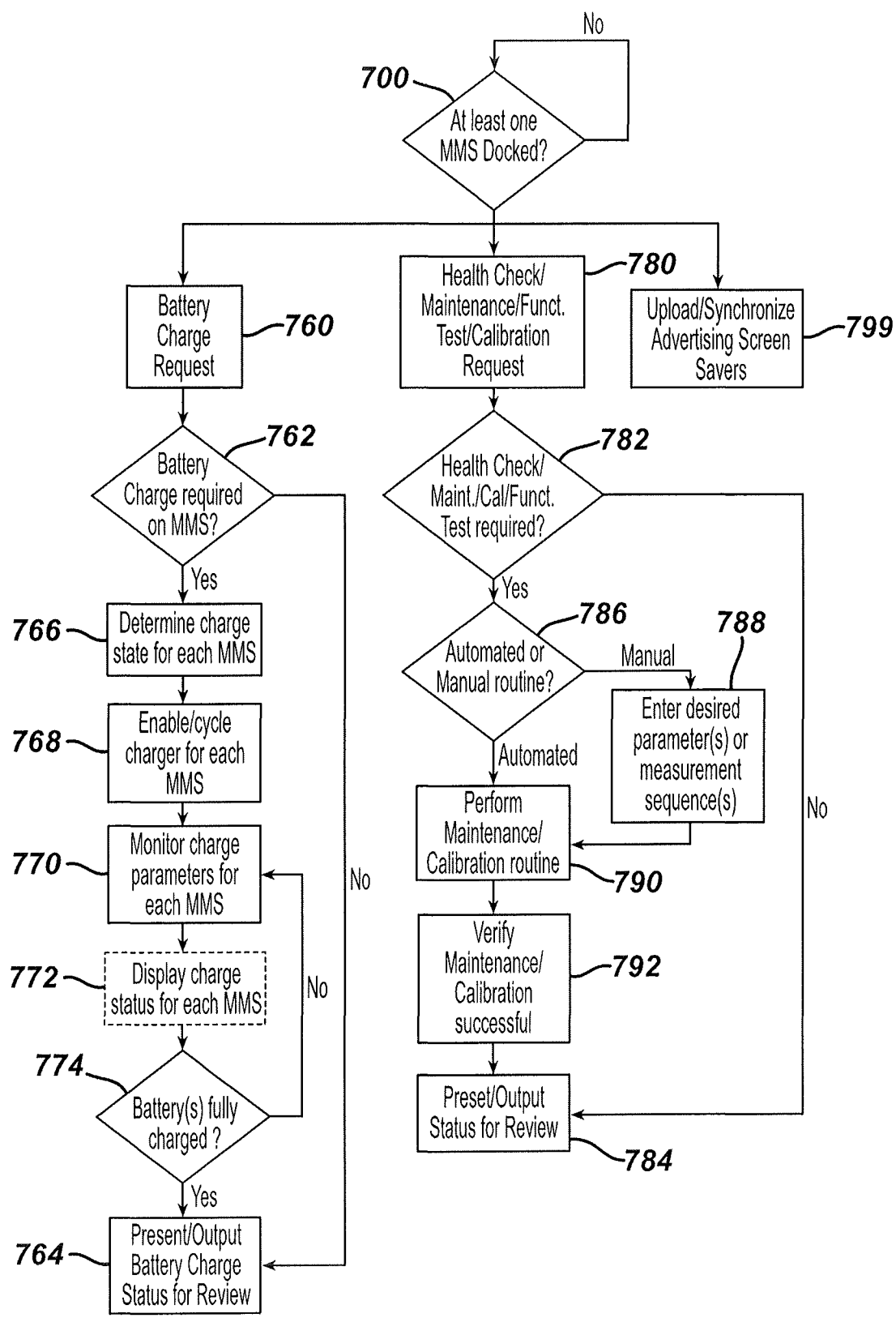
FIG. 12B depicts a flow diagram of another exemplary process that may be carried out using the docking stations of FIGS. 9-11.

FIGS. 12A-12B shows exemplary processes that may be carried out through docking stations (400, 500, 600). It should be understood that at least part of these processes may be carried out by one or more processors of docking stations (400, 500, 600) and/or at least part of these processes may be carried out by one or more processors of BMUs (40). It should also be understood that such processors may include various components, including but not limited to microprocessors, microcontrollers, FPGAs, CPLDs, and/or any other suitable type of hardware or software processing device. As shown in FIGS. 12A-12B, a process may start with a determination as to whether at least one BMU (40) is docked with a docking station (400, 500, 600), step (700). This determination may be made automatically or manually. For instance, the determination may be made automatic by providing one or more sensors in docking station (400, 500, 600) to detect the presence of BMUs (40) being coupled with docking station (400, 500, 600). Similarly, the coupling of BMUs (40) with docking station (400, 500, 600) may simply complete a circuit that activates a feature in response to the circuit being completed. Other suitable ways in which the determination may be made automatically will be apparent to those of ordinary skill in the art in view of the teachings herein. The determination may be made manually by a user informing docking station (400, 500, 600) of the coupling, through user input feature (406, 506, 606) or otherwise.

Once it is determined that at least one BMU (40) is docked with a docking station (400, 500, 600), various other sub-processes may then be carried out. For instance, FIGS. 12A-12B show a configuration data request process, step (710); a stored data request process, step (730); an application software request process, step (740); a battery charge request process, step (760); a diagnostics/calibration request process, step (780); and a screen saver update process, step (799). These sub-processes will be described in greater detail below.

It should be understood that each of these sub-processes is a merely illustrative example, and that each may be substituted, supplemented, varied, or omitted as desired. Various other suitable processes that may be carried out through docking stations (400, 500, 600) will be apparent to those of ordinary skill in the art in view of the teachings herein.

Referring specifically to FIG. 12A, a configuration data request, step (710), may begin with a determination as to whether configuration data should be updated for all BMUs (40) that are coupled with docking station (400, 500, 600), step (712). Such configuration data may include various things, including but not limited to display settings/limits, patient monitoring settings/limits, alarms settings/limits, battery charge settings/limits, battery calibration settings/limits, port settings, RTC clock settings/limits, etc. The determination at step (712) may be made automatically, such as by being based on a selection made when docking station (400, 500, 600) was originally configured/installed; or manually, such as by being based on a selection made by a user via user input feature (406, 506, 606) at step (712) each time the process shown in FIG. 12A is carried out. If all BMUs (40) are not to have their configuration data updated at this stage, then docking station (400, 500, 600) may simply present (e.g., via user interface (404, 504, 604, 42), etc.) or otherwise output data or versions to the user for review, step (714). For instance, step (714) may include presenting the user with information indicating the updated configuration data or version that was available but not uploaded. In addition or in the alternative, step (714) may include presenting the user with information indicating the configuration data or version that remains in BMUs (40) despite the available update. When several BMUs (40) are coupled with docking station (400, 500, 600), and there are differences among the configuration data or versions among those BMUs (40), step (714) may include presenting the user with configuration data or version information on a BMU (40) by BMU (40) basis.

If it is determined at step (712) that all BMUs (40) are to have their configuration data updated, the process next determines whether the same configuration data is desired for all BMUs (40) that are coupled with docking station (400, 500, 600), step (716). Again, this determination may be made automatically, such as by being based on a selection made when docking station (400, 500, 600) was originally configured/installed; or manually, such as by being based on a selection made by a user via user input feature (406, 506, 606) at step (716) each time the process shown in FIG. 12A is carried out. If all BMUs (40) are not to be updated with the same configuration data, then docking station (400, 500, 600) may simply present (e.g., via user interface (404, 504, 604, 42), etc.) or otherwise output data or versions to the user for review, step (714). It should be understood that step (714) may be carried out in the same fashion here as described above; or step (714) may be carried out in some other fashion as will be apparent to those of ordinary skill in the art in view of the teachings herein. It should also be understood that, in some versions, step (712) may permit a user to update only selected BMUs (40) instead of requiring the user to update all BMUs (40) that are coupled with docking station (400, 500, 600) when an update is desired. For instance, a user may wish to differentiate between BMU (40) updates when different BMUs (40) are to be used in different medical procedures, warranting different configuration data. Docking stations (400, 500, 600) may thus permit configuration data updating on a BMU (40) by BMU (40) basis.

If it is determined at step (716) that all BMUs (40) are to be updated with the same configuration data, then the user is prompted to select or enter the preferred configuration (e.g., via user input feature (406, 506, 606), etc.), step (718). With the selection being made, the configuration data is then updated for all BMUs (40) that are coupled with docking station (400, 500, 600), step (720). After the update is complete, then docking station (400, 500, 600) may present (e.g., via user interface (404, 504, 604, 42), etc.) or otherwise output data or versions to the user for review, step (714). It should be understood that step (714) may be carried out in the same fashion here as described above; or step (714) may be carried out in some other fashion as will be apparent to those of ordinary skill in the art in view of the teachings herein.

Still referring to FIG. 12A, a stored data request, step (730), may begin with a determination as to whether data that is stored in BMUs (40) should be synchronized among all of the BMUs (40) that are coupled with docking station (400, 500, 600), step (732). This determination may be made automatically, such as by being based on a selection made when docking station (400, 500, 600) was originally configured/installed; or manually, such as by being based on a selection made by a user via user input feature (406, 506, 606) at step (732) each time the process shown in FIG. 12A is carried out. If the data from one or more BMUs (40) is not to be synchronized among all of the BMUs (40) that are coupled with docking station (400, 500, 600), then docking station (400, 500, 600) may present (e.g., via user interface (404, 504, 604, 42), etc.) or otherwise output data or versions to the user for review, step (714). It should be understood that step (714) may be carried out in the same fashion here as described above; or step (714) may be carried out in some other fashion as will be apparent to those of ordinary skill in the art in view of the teachings herein.

If it is determined at step (732) that data from one or more BMUs (40) is to be synchronized among all of the BMUs (40) that are coupled with docking station (400, 500, 600), then docking station (400, 500, 600) downloads data from all of the BMUs (40) that are coupled with docking station (400, 500, 600), step (734). Such data may include data relating to safety shell operation, data relating to hardware in BMUs (40), data relating to usage of BMUs (40), data relating to PRUs (70) that were coupled with BMUs (40), data relating to patients that were coupled with BMUs (40), and/or any other suitable type of data. Once the data is downloaded (and/or while the data is being downloaded), docking station (400, 500, 600) combines and organizes the data based on specified parameters, step (736). After the data is combined and organized (and/or while the data is being combined/organized), the data is uploaded to all of the BMUs (40) that are coupled with docking station (400, 500, 600) to synchronize the data on BMUs (40), step (738). Then docking station (400, 500, 600) may present (e.g., via user interface (404, 504, 604, 42), etc.) or otherwise output data or versions to the user for review, step (714). It should be understood that step (714) may be carried out in the same fashion here as described above; or step (714) may be carried out in some other fashion as will be apparent to those of ordinary skill in the art in view of the teachings herein. As another merely illustrative example, step (714) in this context may include providing an output of previously stored data such as battery charge history, calibration history, cassette usage, PRU connections, and/or device usage history, etc. Such data may be combined from all BMUs (40) (e.g., when the data has been synchronized through steps (732, 734, 736, 738), etc.) and/or may be provided on a BMU (40) by BMU (40) basis.

As is also shown in FIG. 12A, an application software request process, step (740), may begin with a determination as to whether the software versions are the same in all of the BMUs (40) that are coupled with docking station (400, 500, 600), step (742). This may be performed through a simply query and comparison by docking station (400, 500, 600). After receiving information showing which software versions are on BMUs (40), docking station (400, 500, 600) may also determine whether an upgrade is available for such software, step (744). In some settings, the upgrade will already reside on docking station (400, 500, 600). For instance, docking station (400, 500, 600) may automatically search a network for software upgrades each time docking station (400, 500, 600) is powered on, on some periodic basis, or otherwise. As another merely illustrative alternative, docking station (400, 500, 600) may only search a network for software upgrades when the process reaches step (744). Alternatively, docking station (400, 500, 600) may receive software upgrades in any other suitable fashion.

If no software updates are available, and if it found that software versions on BMUs (40) are different, docking station (400, 500, 600) may synchronize software versions among all BMUs (40). Docking station (400, 500, 600) may prompt a user for confirmation to carry out this step before actually carrying it out. Either way, if software updates are available, docking station (400, 500, 600) may prompt the user to indicate whether the software should be upgraded on BMUs (40), step (746). Such prompting may be provided through user interface (404, 504, 604, 42), and the user's response may be received through user input feature (406, 506, 606). If the user declines to upgrade the software, then docking station (400, 500, 600) may present (e.g., via user interface (404, 504, 604, 42), etc.) or otherwise output data or versions to the user for review, step (714). It should be understood that step (714) may be carried out in the same fashion here as described above; or step (714) may be carried out in some other fashion as will be apparent to those of ordinary skill in the art in view of the teachings herein. For instance, the previous version of the software may be presented to the user to confirm that the upgrade did not occur and that the previous version is still present and fully functional, etc.

If the user elects to upgrade the software, then docking station may upload the new software to all BMUs (40) that are coupled with docking station (400, 500, 600), step (748). Docking station (400, 500, 600) may then optionally verify whether the upgrade was successful on BMUs (40), step (750). If the upgrade was unsuccessful, docking station (400, 500, 600) may repeat the process. If the upgrade was successful, then docking station (400, 500, 600) may present (e.g., via user interface (404, 504, 604, 42), etc.) or otherwise output data or versions to the user for review, step (714). It should be understood that step (714) may be carried out in the same fashion here as described above; or step (714) may be carried out in some other fashion as will be apparent to those of ordinary skill in the art in view of the teachings herein.

Referring now to FIG. 12B, a battery charge request, step (760), may begin with a determination as to whether a battery charge is required in any BMUs (40) that are coupled with docking station (400, 500, 600), step (762). This may be done by simply measuring the amount of charge that is still left in battery (44) of each BMU (40). In making the determination at step (762), docking station (400, 500, 600) may compare the amount of charge for each battery (44) against a predetermined threshold. For instance, docking station (400, 500, 600) may determine that battery (44) needs to be recharged if its power level is below 90%; and that a recharge is not required if the power level is above 90%. Other suitable thresholds and algorithms will be apparent to those of ordinary skill in the art in view of the teachings herein. If it is determined that a battery charge is not required, docking station (400, 500, 600) may present (e.g., via user interface (404, 504, 604, 42), etc.) or otherwise output data to the user indicating that a charge is not needed and/or indicating the charge level for such a battery (44) or batteries (44), step (764).

If it is determined that a battery charge is required, docking station (400, 500, 600) may determine the charge state for each battery (44), step (766); then enable charging circuitry within docking station (400, 500, 600) and/or BMU (40) for each battery (44), step (768). While batteries (44) are charging, docking station (400, 500, 600) may continue to monitor the charge parameters for each battery (44), step (770). If desired, user interface (404, 504, 604) and/or user interface (42) may display the charge status for associated batteries (44) as batteries (44) are being recharged. Such status may be updated in real time or near-real time. Docking station (400, 500, 600) may repeatedly determine whether batteries (44) are fully charged, step (774). If batteries (44) are not fully charged, docking station (400, 500, 600) may continue charging batteries (44) until they are fully charged (or at least sufficiently charged). Once docking station (400, 500, 600) determines that batteries (44) re fully charged, docking station (400, 500, 600) may present (e.g., via user interface (404, 504, 604, 42), etc.) or otherwise output data to the user indicating that batteries (44) are fully charged, step (764).

As is also shown in FIG. 12B, a diagnostics/calibration request process, step (780), may begin with a determination as to whether a diagnostics/calibration test is required. Such a test may be used to determine whether the hardware, software, etc. of BMUs (40) is in proper working order and/or to ensure that the same is calibrated properly. In some versions, the determination of whether a test is required is based on passage of time since the test was last performed. For instance, docking station (400, 500, 600) may track instances of such testing being performed, and may include a logic that indicates testing is necessary on some predefined periodic basis. Other suitable ways for automating the determination will be apparent to those of ordinary skill in the art in view of the teachings herein. Alternatively, docking station (400, 500, 600) may prompt the user to indicate whether the user wishes for docking station (400, 500, 600) to perform diagnostics/ calibration. Either way, if it is determined that a diagnostics/ calibration test is not required, docking station (400, 500, 600) may simply present (e.g., via user interface (404, 504, 604, 42), etc.) or otherwise output to the user an indication that a diagnostics/calibration test is not required, step (784).

If it is determined that a diagnostics/calibration test is required, docking station (400, 500, 600) may determine whether the test/calibration will be carried out based on manual inputs or based on a purely automated sequence, step (786). If the test/calibration is to be carried out based on manual input, the user then enters the desired parameters, etc., for the test/calibration, such as through user input feature (406, 506, 606), step (788). Regardless of whether the test/ calibration is carried out based on manual inputs or based on a purely automated sequence, docking station (400, 500, 600) performs the test/calibration on BMUs (40) that are coupled with docking station, step (790). After the test/calibration is complete, docking station (400, 500, 600) verifies the success of the test/calibration, step (792). If the test/calibration was unsuccessful, the test/calibration is repeated. After the success of the test/calibration has been verified, docking station presents (e.g., via user interface (404, 504, 604, 42), etc.) or otherwise outputs to the user an indication that a diagnostics/ calibration test is complete, step (784).

FIG. 12B also shows a screen saver update process, step (799), that may be carried out upon a determination that one or more BMUs (40) are coupled with docking station (400, 500, 600). This sub-process may be used when one or more user interfaces (404, 504, 604, 42, 72) are operable to display a screen saver or other type of visual rendering that does not necessarily relate to medical data. For instance, such a screen saver or other type of visual rendering may comprise an advertisement, etc. Thus, the screen saver update process may be used to update screen savers across all BMUs (40) that are coupled with docking station (400, 500, 600). For instance, docking station (400, 500, 600) may receive screen saver updates from a network on any suitable basis, and may transmit one or more of such screen savers to BMUs (40) automatically upon coupling of BMUs (40) with docking station (400, 500, 600). As another merely illustrative example, docking station (400, 500, 600) may have a plurality of screen savers already stored thereon, and may pull from those pre-saved screen savers to update screen savers of BMUs (40) on a periodic basis. Of course, as with other processes described herein, a screen saver update process may simply be omitted (e.g., in versions where screen savers are not used or cannot be changed, etc.). Still other suitable processes that may be carried out through docking stations (400, 500, 600) will be apparent to those of ordinary skill in the art in view of the teachings herein.

B. Exemplary Centralized Control Unit for Remote Monitoring and Control of PRUs

Figure 13:
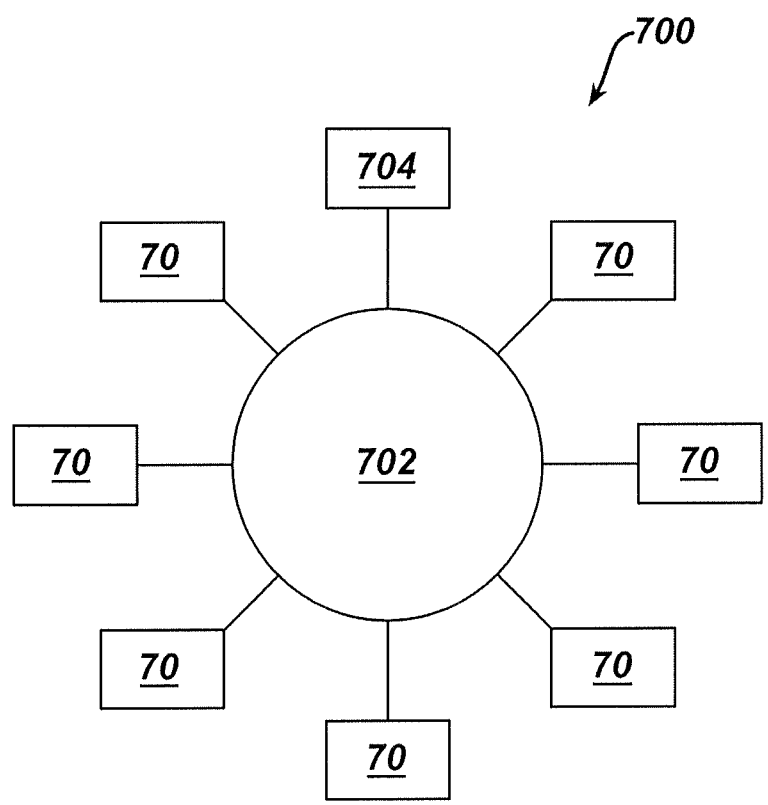
FIG. 13 depicts a block schematic diagram of several drug delivery systems with an exemplary centralized management unit.

FIG. 13 shows an exemplary system (700) where a plurality of PRUs (70) are coupled with a central station (702). Central station (702) may include a server and/or other computer related hardware components that are in communication with PRUs (70) via a network. For instance, such communication may be provided via cables and/or wirelessly. It should also be understood that central station (702) may be coupled with one or more other devices or systems (704), such as a hospital's patient medical record database, etc. In some versions, a person such as an anesthesiologist sits at central station (702) and is able to simultaneously monitor and/or at least partially control operation of several PRUs (70) via central station (702). It is contemplated that some versions of central station (702) may not have a fixed or predetermined geographic location. For instance, some versions of central station (702) may comprise a smartphone or other portable electronic device that is carried by an anesthesiologist or other person. In addition or in the alternative, central station (702) may be provided through a secure web interface or other portal that is accessible from various locations. Thus, references herein to a person being "at" a central control station (702) should not be read as requiring central control station (702) to be at a fixed location or at a predetermined location, etc.

In the present example, central station (702) provides a unified display of operation of PRUs (70). For instance, central station (702) may allow a user to selectively view data associated with each PRU (70) individually, such as by flipping through one or more windows or screens associated with each PRU (70). For instance, central station (702) may allow a user to view data showing how each PRU (70) is operating, in real time. Central station (702) may also provide a vehicle to review historical data relating to use of PRUs (70), data relating to alarms provided through PRUs (70), etc. In addition to showing data relating to each PRU (70) individually, central station (702) may also allow a user to view data associated with PRUs (70) collectively. For instance, central station (702) may process data received from each PRU (70) and provide a report showing averages, trends, and/or other collective information that is based on data from several PRUs (70).

Similarly, central station (702) may provide a unified display of data from BMUs (40) (e.g., from BMUs (40) that are coupled with the PRUs (70) of central station (702), etc.). Thus, a person at central station (702) could monitor physical parameters of patients that are coupled with BMUs (40) while also monitoring the delivery of drugs oxygen, etc. from PRUs (70). In addition or in the alternative, central station (702) may present a user with other patient information (e.g., identity of patients coupled with BMUs (40), demographics of patients coupled with BMUs (40), excerpts and/or reminders from the records of patients coupled with BMUs (40), etc.); what medical procedures are being performed on patients coupled with BMUs (40); which clinical team (e.g., doctor, nurse, etc.) is in the room with each BMU (40); and/or various other kinds of information. As with data from PRUs (70), data from BMUs (40) may be presented to a user at central station (702) in relation to each BMU (40) individually and/or as collective information in relation to a plurality of BMUs (40). One or more cameras could also be used to provide a user at central station (702) with streaming video from each room in which each BMU (40) is located, enabling the user at central station (702) to view each medical procedure in real time.

Central station (702) of the present example may also be used to control one or more PRUs (70) from a centralized location. For instance, control station (702) may be used to override a safety shell control algorithm of a PRU (70), to stop the delivery of a drug that would otherwise be delivered through PRU (70) pursuant to the safety shell, to increase delivery of oxygen through PRU (70), to change parameters and/or safety profiles for a PRU (70), to change the delivery rate of one or more drugs by a PRU (70), and/or to otherwise change the operation of PRU (70). In some such versions, central station (702) may notify the user of PRU (70) (e.g., the clinician) that such action has been taken remotely. In addition, in some such versions, control by the operator at the central station (702) may be restricted, such that the operator at central station (702) may only reduce drug delivery by a PRU (70); and may not increase drug delivery by a PRU (70). A user at control station (702) may also set alarm levels in PRU (70), otherwise modify a safety shell control algorithm in PRU (70), and/or receive and respond to an alarm that has been triggered in a PRU (70).

As another merely illustrative example, PRUs (70) may be provided with a two-mode safety shell. For instance, one mode may be configured for operation of PRUs (70) by a non-anesthesiologist (e.g., by a clinician/nurse team). In this mode, the safety shell may impose certain limits on operation of PRU (70), such as limits on drug delivery, and/or may provide a different sensitivity to patient responsiveness. A second mode may be configured for operation of PRUs (70) by an anesthesiologist sitting at control station (702). In some versions of such a second mode, the anesthesiologist at control station (702) may control PRU (70) as a standard drug infusion pump (e.g., propofol infusion pump), without being subject to drug delivery limitations imposed under the first mode. The anesthesiologist may be provided with a capability at control station (702) to switch a given PRU (70) from the first mode of the safety shell to the second mode of the safety shell, and vice-versa. In some such versions, the second mode of the safety shell will only allow PRU (70) to be switched back to the first mode of the safety shell when the patient's physical parameters have returned to or otherwise reached a certain state (e.g., the patient has stabilized), based on data from BMU (40).

In versions where control station (702) provides enhanced functionality to anesthesiologists (e.g., the second mode referred to above, etc.), control station (702) may include a feature for confirming the identity of the anesthesiologist. For instance, control station (702) may include a biometric identification feature (e.g., a fingerprint reader, retinal scanner, etc.); password protection; a manual key switch; an RFID tag; an EAS tag; a magnetic, optical, or physical card swipe, etc. In versions sensitive to the presence of an RFID tag or similar type of device that is detectable through proximity to a sensor, control station (702) may be configured to automatically switch back to a more restrictive mode (e.g., the first mode referred to above) as soon as the anesthesiologist leaves control station (702).

Central station (702) may also be used to communicate with patients, nurses, clinicians, and/or other persons via PRU (70). For instance, a person at central station (702) may send text messages, video messages, streaming video, etc., to display screen (72) of at least one selected PRU (70). In addition or in the alternative, a person at central station (702) may communicate audio to another person through at least one selected PRU (70). PRU (70) may also enable a person at PRU (70) to initiate a textual, video, and/or audio discussion with a person at central station (702), such as when a nurse or clinician at PRU (70) needs assistance from an anesthesiologist, etc. As yet another merely illustrative example, central station (702) may enable a person at BMU (40) and/or PRU (70) to query central station (702) to obtain information such as patient data, next steps in the medical procedure, etc. Still other suitable components, features, and functionalities that may be incorporated into or provided by a central station (702) will be apparent to those of ordinary skill in the art in view of the teachings herein.

IV. Exemplary Additional Inputs for PRU

As described in detail above, PRU (70) receives input from BMU (40) relating to real time physiological conditions of the patient. This data is processed through the safety shell control algorithm of PRU (70) to regulate drug delivery to the patient, to provide alerts and other information to a clinician and/or nurse, and/or for other purposes. It should also be understood that a PRU (70) may receive various other kinds of inputs. Some examples of such additional inputs will be described in greater detail below, while still other examples will be apparent to those of ordinary skill in the art in view of the teachings herein. As will also be apparent in view of the teachings herein, additional inputs for a PRU (70) may be provided manually or automatically. For instance, manual inputs may be manually provided by a user (e.g., a nurse or clinician, etc.) via touch screen assembly (72), via drug delivery controls (74), via a central station (702), and/or otherwise. Inputs may be provided automatically from BMU (40), from one or more ancillary devices (e.g., any of those referred to above in the context of system (300), etc.), from central station (702), and/or from some other source.

In some versions of PRU (70), touch screen (72) is capable of presenting a subset of options, icons, widgets, or the like at any given moment of operation. When presented with these, a user may select one in order to activate PRU (70) to perform some kind of action. For instance, a set of options, icons, widgets, etc. may include those associated with updating PRU (70), delivering a drug, contacting a person at central station (702), etc. Touch screen (72) may selectively change the options, icons, widgets, etc. that are presented, based at least in part on one or more inputs into PRU (70). For instance, a user may actuate a drug delivery icon, which may cause touch screen (72) to display additional options, icons, widgets, etc., associated with specific kinds of drugs. As another merely illustrative example, real time patient data from BMU (40) may change the options presented to a user via touch screen (72). Various other suitable ways in which options, icons, widgets, etc. may change and operate, as well as various types of inputs that may control the presentation of options icons, widgets, etc., will be apparent to those of ordinary skill in the art in view of the teachings herein.

A. Exemplary Input Relating to Administration of External Drug

As described above, some versions of PRU (70) may be intended to simplify the delivery of drugs to a patient, such as by either minimizing the role of real-time human judgment or eliminating the role of real-time human judgment in the selection of the amount of drug to be delivered, type of drug to be delivered, duration of drug delivery, etc. Some versions of PRU (70) also simplify the delivery of drugs to a patient by containing all of the drugs that are needed in a drug cassette (84). However, there may be instances where it is desired to deliver one or more drugs to a patient from a source that is external to PRU (70). For instance, an anesthesiologist may determine based on data from BMU (40), based on a particular patient's unique medical history or dispositions (e.g., diabetes requiring insulin injection), and/or based on other considerations that the patient should receive a dose of a certain drug (e.g., an analgesic, etc.) that is not contained in drug cassette (84). In such situations, it may be desirable to provide a means to inform PRU (70) that this drug is being delivered to the patient. That way, the safety shell control algorithm in PRU (70) may account for the delivery of that "external" drug and make appropriate adjustments. Such adjustments may affect subsequent drug delivery by PRU (70), physiological parameters monitored by BMU (40), conditions that will trigger an alarm, etc. Various suitable ways in which PRU (70) may respond to an indication that an external drug is being delivered and/or has been delivered will be apparent to those of ordinary skill in the art in view of the teachings herein.

It should also be understood that PRU (70) may be informed of the delivery of an external drug in a variety of ways. For instance, PRU (70) may include an additional one or more buttons through which such input may be provided. In addition or in the alternative, touch screen (72) may receive inputs indicating the delivery of an external drug. In some versions, the user activates a button or touch screen (72), etc., to indicate that an external drug is going to be delivered or has been delivered. Touch screen (72) then presents the user with options to further indicate the type of drug to be delivered, the amount of drug delivered, etc.

In some versions, an "external drug" is one that is not contained in drug cassette (84), such that the drug is external to PRU (70). For instance, an external drug maybe contained in a separate syringe, in an IV solution delivery system (352), etc. In addition or in the alternative, an "external drug" may include one that is contained in drug cassette (84) but whose selection, timing of delivery, duration of delivery, and/or some other aspect of administration is outside the scope of the currently running safety shell control algorithm. For instance, if a safety shell control algorithm would normally only have a certain drug delivered when only a certain set of circumstances are present, and would normally only deliver a certain amount of that drug, it may be considered an external delivery of a drug where a person essentially overrides the safety shell and causes the drug to be delivered from drug cassette (84) at a different time and/or for a different duration, etc. In either type of external drug delivery, the safety shell control algorithm may be adaptive and be thereby capable of adjusting subsequent drug delivery, subsequent triggering of alarms, etc., taking the external drug delivery into account. Various suitable changes that may be made in a safety shell control algorithm and/or other types of accommodations that can be made based on the delivery of an external drug will be apparent to those of ordinary skill in the art in view of the teachings herein.

B. Exemplary Input Relating to Stage of Medical Procedure

Specific examples of PRU (70) inputs discussed above include real time patient related data from BMU (40) and information regarding the delivery of one or more external drugs. As described above, these inputs can affect subsequent delivery of drugs, triggering of alarms, and other processes carried out through PRU (70) in accordance with a safety shell control algorithm. Another exemplary type of input that may affect one or more processes carried out through PRU (70) in accordance with a safety shell control algorithm may include an indication of the type of medical procedure a patient is undergoing. Similarly, an input indicating the current stage of a medical procedure may affect one or more processes carried out through PRU (70) in accordance with a safety shell control algorithm. By way of example only, at the beginning of a procedure, touch screen (72) may present a user with a list of various types of medical procedures. The user may thus interact with touch screen (72) to select the type of medical procedure that PRU (70) will be used in. A catalog of various kinds of procedures may be preloaded in PRU (70), may be transmitted to PRU (70) from BMU (40) (which may have received updates to the catalog through a docking station (400, 500, 600)), may be transmitted to PRU (70) from central station (702), and/or may be otherwise received by PRU (70).

Once a user informs PRU (70) of the type of medical procedure in which PRU (70) will be used, touch screen (72) may present the user with a listing of different key stages of that procedure, in sequence. As the medical procedure advances through those stages, the user can manually "tick off" those stages through interactions with touch screen (72) and/or may otherwise inform PRU (70) of the initiation and/or completion of each stage, as each stage is being initiated and/or completed. The safety shell control algorithm in PRU (70) may be configured to respond to the initiation and/or completion of each stage accordingly. Examples of such responses in the context of a colonoscopy and an esophagogastroduodenoscopy (EGD) will be described in greater detail below, while other examples will be apparent to those of ordinary skill in the art in view of the teachings herein.

Figure 14:
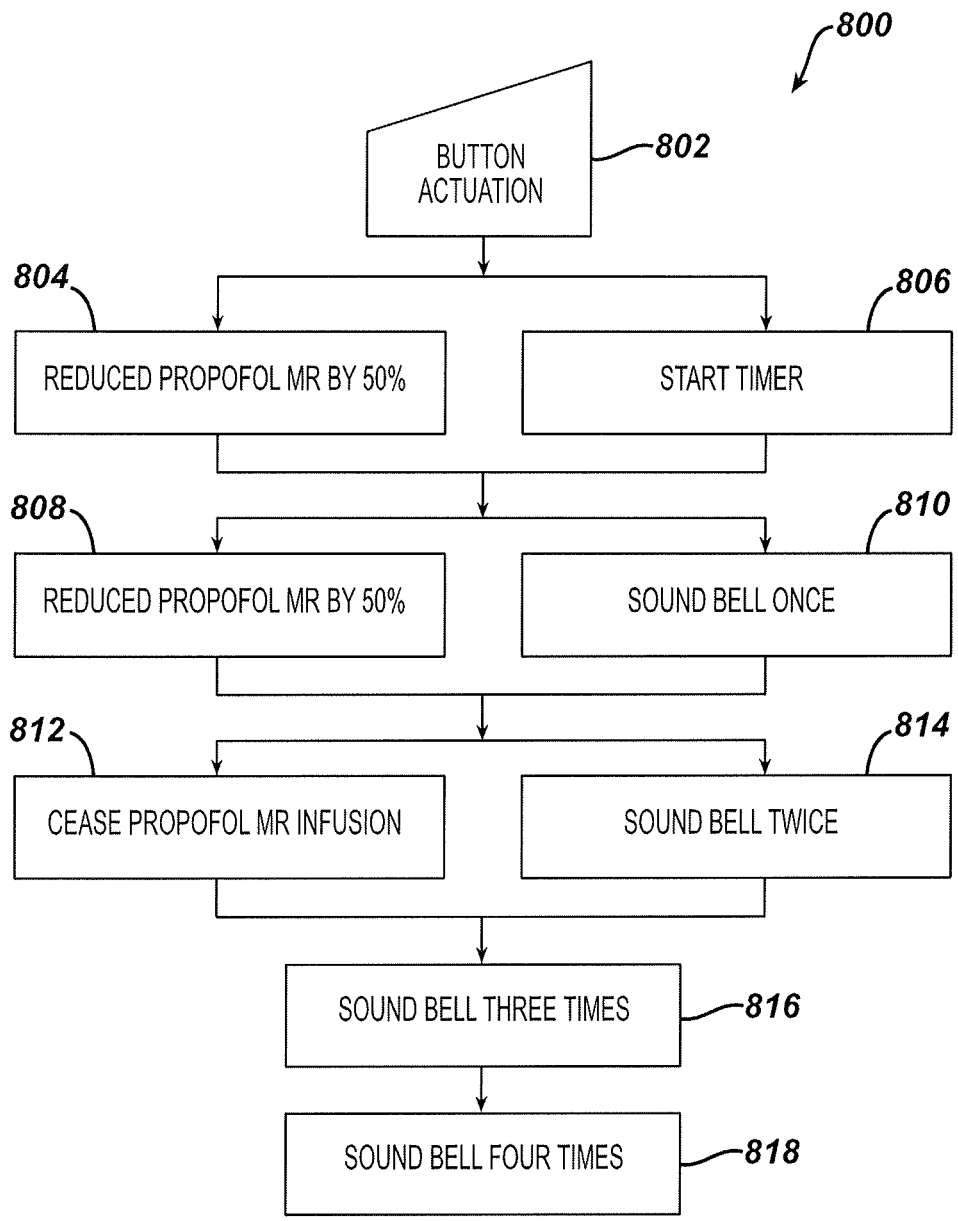
FIG. 14 depicts a flow diagram of an exemplary process that may be carried out using the system of FIG. 1.

FIG. 14 shows an example of how a safety shell control algorithm may respond to input that a colonoscopy has reached a certain stage. In particular, this exemplary method (800) may encourage an endoscopist to take more time to examine a colon as the endoscope is being withdrawn from the colon, which may in turn result in an increase in the detection of polyps in the colon. In addition, this method (800) may reduce the delivery of sedation to the patient during withdrawal of the endoscope from the colon, which may in turn improve patient recovery time. After the endoscopist has reached the patient's cecum with the endoscope, the endoscopist may actuate a button on PRU (70) (e.g., on touch screen (72), etc.), or instruct a nurse to actuate the button, to indicate that the endoscope has reached the cecum, step (802). In response to this input, PRU (70) simultaneously reduces delivery of a drug such as propofol by 50%, step (804); and starts a timer, step (806). PRU (70) then tracks the passage of time with the timer. When two minutes have passed, the safety shell causes PRU (70) to simultaneously reduce propofol delivery by 50%, step (808); and sound a bell or other audible alert once, step (810). PRU (70) continues to track the passage of time with the timer. After an additional two minutes have passed (i.e., four minutes from when the button was pressed in step (802)), the safety shell causes PRU (70) to simultaneously cease delivery of propofol, step (812); and sound a bell or other audible alert twice, step (814). After another two minutes have passed (i.e., six minutes from when the button was pressed in step (802)), the safety shell causes PRU (70) to sound a bell or other audible alert three times, step (816). After yet another two minutes have passed (i.e., eight minutes from when the button was pressed in step (802)), the safety shell causes PRU (70) to sound a bell or other audible alert four times, step (818). The endoscopist may be trained to avoid fully withdrawing the endoscope from the patient until the endoscopist has heard the bell or other audible alert sound four times. This may ensure that the endoscopist takes at least eight minutes to withdraw the endoscope. In the foregoing example, PRU (70) receives input from the user (step (802)) and from the timer, though it should be understood that other inputs may be used.

In certain settings, such as those where a patient has greater sensitivity to pain, the above described drug delivery reductions (steps (804, 808, 812)) may not be ideal. In such situations, PRU (70) may allow the clinician to deliver a PRN drug dose and/or allow the clinician to adjust the reductions in delivery of propofol or some other drug. It should also be understood that the above described method (800) may be modified in various ways, even for a colonoscopy. For instance, PRU (70) may enable a user to program the safety shell to provide longer increments between soundings of the bell, provide more frequent soundings of the bell, adjust the frequency and/or amounts of reductions in delivery of propofol or other drugs, or otherwise modify the method (800) based on user defined parameters. It should also be understood that the above described method (800) and variations thereof may be readily applied to other procedures, such as an EGD procedure. For instance, step (802) may be carried out when an endoscope reaches a patient's duodenum, thereby initiating performance of the method (800). The method (800) may also be readily adapted to settings where more than one procedure is performed, such as an EGD followed by a colonoscopy. Various other types of procedures in which the teachings herein may be readily applied will be apparent to those of ordinary skill in the art in view of the teachings herein.

In the examples described herein, a user manually informs PRU (70) of the initiation and/or completion of each key stage in a medical procedure, such as by interacting with touch screen (72) or otherwise. In some other versions, PRU (70) may be automatically informed about the initiation and/or completion of one or more stages of a medical procedure, such as in examples of system (300) described above where additional ancillary devices are in communication with PRU (70). For instance, an endoscope may include one or more exterior photosensors positioned along its length. Such photosensors may be used to sense the depth of insertion of the endoscope in the patient and/or to determine the direction of axial movement of the endoscope relative to the patient, based on how much length of the endoscope is exposed to light by being external to the patient. This information on endoscope positioning may be interpreted as being indicative of the stage of a surgical procedure (e.g., detected withdrawal of endoscope indicates procedure nearing conclusion, etc.), and the safety shell may react accordingly. Similarly, and referring back to the above examples of colonoscopy and EGD, such information on endoscope positioning may be used to alert a user when an endoscope is being withdrawn from a patient too quickly.

As another merely illustrative example, continuing with the context of system (300) described above, data from a therapeutic instrument (322) that is coupled with PRU (70) may be interpreted by PRU (70) to indicate completion or initiation of a stage in a medical procedure. For instance, PRU (70) may simply sense when a therapeutic instrument (322) has been activated, which may be interpreted to mean that a particular stage of a procedure has begun. Various other suitable ways in which a PRU (70) may be automatically informed of progress in stages of a medical procedure will be apparent to those of ordinary skill in the art in view of the teachings herein. In versions where PRU (70) is automatically informed of progress in a medical procedure, touch screen (72) may still present a pop-up or similar prompt to the user, seeking confirmation that the stage has in fact been initiated and/or completed. It should also be understood that medical stage inputs for PRU (70) may be provided both manually and automatically in certain versions. For instance, some stages of a given procedure may be input manually while other stages of the same procedure are input automatically.

C. Exemplary Inputs Relating to Patient Data Points

While the above description of BMU (40) includes several patient physical parameters that may be detected by BMU (40) and may be thereby transmitted to PRU (70), it should be understood that other kinds of patient data may be provided as inputs for PRU (70), in addition to or in lieu of those kinds of patient data referred to above. Such additional patient data may be captured using one or more accessories of BMU (40), using one or more accessories that are coupled with PRU (70) as an ancillary device, or otherwise. One additional form of patient data may include data relating to the patient's respiratory quotient (RQ), which is the ratio of carbon dioxide volume removed from the body to the oxygen volume consumed by the body. By way of example only, one or more RQ monitoring components from CardioPulmonary Technologies, Inc. of Sussex, Wis. may be incorporated into BMU (40) or otherwise be placed in communication with PRU (70). Alternatively, any other suitable components may be used to obtain RQ data.

In some versions, a safety shell control algorithm may monitor RQ instead of respiratory rate, since RQ may be an earlier predictor of respiratory compromise in some settings. Of course, a safety shell control algorithm may monitor both RQ and respiratory rate, if desired, as well as respiratory sounds, pressure, temperature, and/or other parameters associated with respiration. Various suitable ways in which these other parameters associated with respiration may be monitored will be apparent to those of ordinary skill in the art in view of the teachings herein. A safety shell control algorithm may be configured to provide alerts based at least in part on RQ levels and/or trends in RQ; and/or to regulate delivery of drugs and/or oxygen to the patient based at least in part on RQ levels and/or trends in RQ. Various other suitable ways in which a safety shell control algorithm may respond to RQ data will be apparent to those of ordinary skill in the art in view of the teachings herein.

It should also be understood that RQ data may be reviewed in order to determine the suitability of using PRU (70) for a particular patient. For instance, if RQ data indicates that a patient is a relatively poor breather (having low quality of breathing), a clinician may decide to not use PRU (70) with that patient. RQ data may thus be used by the clinician to exercise judgment in the operation of PRU (70). In other words, RQ data need not be limited to use in a safety shell control algorithm. Furthermore, it should be understood that it may be desirable to account for delivery of oxygen by PRU (70) when calculating RQ data, to ensure that the RQ is not rendered inaccurate by the delivered oxygen. PRU (70) may thus adjust the RQ based on when the patient is inhaling and the level of oxygen being provided to the patient.

As another merely illustrative example, PRU (70) may receive inputs relating to the patient's medical history (e.g., prior procedural history, current and previous medications, etc.), weight, gender, age, ethnicity, etc., and this information may also influence the selection of a safety shell control algorithm and/or the execution of a safety shell control algorithm. This information may allow the development of a more complete and accurate risk profile for a given patient, particularly the patient's risk to sedation. In other words, this information may be used to provide a risk input. At least some of this type of information may be entered into BMU (40) by a nurse or clinician as part of the process shown in FIG. 5. In addition or in the alternative, at least some of this type of information may be entered into BMU (40) and/or directly into PRU (70) as part of the process shown in FIG. 6. It should also be understood that the information may be entered manually (e.g., via touch screen (42, 72), etc.), via a memory card, via a network (e.g., from central station (702) and/or from a hospital's medical records database, etc.), or otherwise. Various other suitable ways in which such information may be provided to PRU (70) will be apparent to those of ordinary skill in the art in view of the teachings herein.

It should be understood that information relating to a patient's medical history, weight, gender, age, ethnicity, etc., may influence a safety shell control algorithm in various ways. For instance, such information may affect the selection of drugs delivered through the safety shell, the amount of drugs delivered through the safety shell, the timing of drug delivery through the safety shell, the duration of drug delivery through the safety shell, the conditions that will trigger an alert, the sensitivity of alert triggers, etc. Thus, the safety shell can determine where a patient lies on a risk continuum, based on information relating to a patient's medical history, weight, gender, age, ethnicity, etc.; and then adapt the safety shell based on where the patient lies on the risk continuum. By way of example only, PRU (70) may automatically reduce drug delivery for patients whose weight is below a certain threshold, for female patients, for patients with a known sensitivity to drugs, etc. As another merely illustrative example, if PRU (70) receives an input indicating that a patient is regularly taking a prescribed drug that makes the patient resistant to anesthetics (e.g., patient is taking serotonin reuptake inhibitor (SRI), etc.), PRU (70) may automatically allow a higher initial maintenance rate of drug delivery and/or allow higher drug delivery maintenance rate increases to allow for adequate levels of sedation. As another merely illustrative example, the above noted risk related information may influence alert settings of PRU (70), such as by making such alerts more sensitive to one or more monitored physiological conditions based in part on the risk profile. Similarly, the above noted risk related information may influence drug delivery limit settings of PRU (70), such as by reducing such limits based in part on the risk profile. Other suitable responses to risk profile information as discussed above will be apparent to those of ordinary skill in the art in view of the teachings herein.

It should also be understood that a patient's location on a risk profile may change during a medical procedure. For instance, if BMU (40) detects conditions indicating a desaturation or apnea episode, the patient's risk level on the continuum may be increased. An increase in risk level may increase the sensitivity of alarms and/or increase restrictions on drug delivery through the safety shell. Conversely, if the patient has no adverse effects over a period of time during a medical procedure, the patient's risk level on the continuum may be decreased. Still other suitable inputs that may be used to influence a safety shell, as well as various ways in which such inputs may influence a safety shell, will be apparent to those of ordinary skill in the art in view of the teachings herein.

V. Exemplary Audible Outputs

As noted above, a safety shell control algorithm may provide one or more alerts as a response to a certain condition or combination of conditions. Such alerts may be triggered through BMU (40) and/or through PRU (70). In some instances, the alerts may be directed to a physician/clinician/nurse/anesthesiologist/etc. In addition or in the alternative, alerts may be directed to the patient. The following will discuss several merely illustrative examples of alerts that may be provided through system (10), though other types of alerts will be apparent to those of ordinary skill in the art in view of the teachings herein. In addition, while the examples below relate mainly to audible alerts, it should be understood that alerts may also be provided visually (e.g., through screen (42), through screen (72), and/or otherwise). Other various ways in which alerts may be provided will be apparent to those of ordinary skill in the art in view of the teachings herein.

A. Audible Alerts as Verbal Expressions

In some instances, alerts are provided to a user (e.g., physician/clinician/nurse/anesthesiologist/patient/etc.) in the form of audible tones. In some such versions, different alerts may be communicated by tones having different timbres, different patterns, different durations, different volumes, and/or other different properties. The user may thus learn these differences before using system (10), in order to be able to readily interpret the meaning of these different tones during subsequent use of system (10). Similarly, some versions of system (10) may play an audible tone when an alert condition (or combination of conditions) has cleared and/or in various other circumstances. For instance, after an alert has cleared, system (10) may emit an audible tone to indicate that PRU (70) has started drug delivery again.

In addition to or in lieu of having system (10) emit audible tones in various circumstances, system (10) may be configured to emit verbal instructions. For instance, system (10) may provide a verbal instruction to the patient to press a button on handpiece (62) or otherwise interact with handpiece (62). As another merely illustrative example, system (10) may verbally instruct the patient to "take a deep breath." In some instances, verbal instructions and/or other verbal messages are provided to a patient via earpiece (60). In addition or in the alternative, verbal instructions and/or other verbal messages may be provided to a patient via a speaker in BMU (40), a speaker in PRU (70), and/or otherwise.

In the context of verbal instructions and/or other verbal messages to a non-patient, system (10) may verbally instruct the physician/clinician/nurse/etc. to "resume propofol infusion" after an alert has cleared. As yet another merely illustrative example, system (10) may verbally advise the physician/clinician/nurse/etc. that "it is now safe to restart the maintenance rate." Other verbal instructions/messages may relate to one or more of the following: notification of whether the patient successfully completed automated ART training (from step (210) of FIG. 5); alarm conditions with respect to patient physiology; basic patient physiometrics that may be provided on a periodic basis (e.g., heart rate, blood pressure, respiration rate, etc.); system advisories with instructions on how to correct fault conditions; other system related information such as when a printout is occurring and changes made to settings; drug changes made to the system or by the system; notification of when a loading dose is complete; and/or notification of when a PRN dose is available again. Other various verbal instructions and/or other messages that system (10)

may provide to a physician/clinician/nurse/anesthesiologist/patient/etc. will be apparent to those of ordinary skill in the art in view of the teachings herein.

It should be understood that using verbal instructions/messages instead of audible tones may prevent the user of system (10) from having to learn and memorize the meaning of various abstract audible tones. It should also be understood that meaningful audible alerts may better enable the physician/clinician/nurse/anesthesiologist/etc. to focus on the patient, without the physician/clinician/nurse/anesthesiologist/etc. having to focus as much on a screen (42, 72) for visual alerts, though audible alerts may of course be supplemented or substituted with visual alerts on screen (42, 72) if desired.

B. Audible Alerts via Earpiece

In some versions of system (10), audible alerts (e.g., tones, verbal instructions, verbal messages, etc.) are provided through speakers such that the alerts may be heard by various people within the procedure room. For instance, BMU (40) and/or PRU (70) may include one or more speakers that are configured to emit such alerts. In addition or in the alternative, alerts may be provided to a physician/clinician/nurse/etc. via an earpiece. Such alerts may include various audible tones as discussed above. In addition or in the alternative, such alerts may include verbal instructions/messages as discussed above. Such an earpiece may be in communication with BMU (40) and/or PRU (70) via one or more wires and/or wirelessly (e.g., Bluetooth, etc.). In some versions, the earpiece is also capable of communicating other types of audio. For instance, the earpiece may also be part of a precordial stethoscope system, such that the earpiece is capable of communicating both the sound of the patient's heartbeat and/or breathing as well as various alerts from system (10). As noted above with respect to audible alerts in general, alerts through an earpiece may better enable the physician/clinician/nurse/anesthesiologist/etc. to focus on the patient, without the physician/clinician/nurse/anesthesiologist/etc. having to focus as much on a screen (42, 72) for visual alerts, though audible alerts through an earpiece may of course be supplemented or substituted with visual alerts on screen (42, 72) if desired.

C. Audible Tone to Alter Heartbeat of Patient

As noted above, BMU (40) may be configured to monitor a patient's heartbeat, respiration rate, and/or other physiological conditions. This data may be communicated to PRU (70) and thereby be processed through a safety shell control algorithm executed through PRU (70). In addition or in the alternative, a safety shell control algorithm may be executed through BMU (40). In some instances, such as when a sedative is administered to the patient, the patient's heart rate may fall below a predetermined threshold (e.g., bradycardia), may define an erratic pattern, and/or may otherwise demonstrate undesirable characteristics. It may be desirable to take appropriate action in such circumstances in order to correct the patient's heart rate. One way in which this may be done is to communicate a tone pulse to a patient, such as at a constant beat per minute, in order to influence the patient's heart rate. For instance, the tone pulse rate may be faster that the patient's measured heart rate. In some instances, this communication of a faster tone pulse rate to the patient may influence the patient's heart rate, such as by causing the patient's heart rate to increase and/or stabilize.

In the present example, the safety shell is configured such that a tone pulse pattern will be communicated to the patient as soon as the patient's heart rate falls below sixty beats per minute. Of course, any other suitable threshold may be used to trigger a tone pulse pattern. Similarly, a combination of conditions and/or trend in conditions may be required in order to trigger a tone pulse pattern. The tone pulse rate may be a predetermined number (e.g., seventy tone pulses per minute, etc.). Alternatively, the tone pulse rate may be a function of the patient's heart rate (e.g., 110% of the patient's measured heart rate, etc.). It should also be understood that the tone pulse rate may change as the patient's heart rate changes. In such versions, the tone pulse rate may increase, as the patient's heart rate increases, until the tone pulse rate reaches a certain level and/or until the patient's heart rate reaches a certain level. The amplitude and/or sonic frequency of the tone may also change in addition to the tone pulse rate changing. For instance, if the patient's heart rate fails to respond to the tone pulse pattern (e.g., the patient's heart rate continues to drop despite the tone pulse pattern), the amplitude and/or sonic frequency of the tone may increase in order to increase the external stimulus to the heart rate.

In versions where a tone pattern is communicated to a patient in order to influence the patient's heart rate, there are various ways in which the tone pattern may be communicated to the patient. For instance, a tone pattern may be communicated to the patient via earpiece (60). Alternatively, a tone pattern may be communicated to the patient via a speaker in BMU (40) or a speaker in PRU (70). Various other suitable ways in which tone patterns may be implemented in system (10) will be apparent to those of ordinary skill in the art in view of the teachings herein.

D. Alerts Based on Trends in Data

In some versions of system (10), a safety shell control algorithm is based on comparisons between patient physiological data from BMU (40) against predefined discrete thresholds. The relationship between the value of a particular physiological parameter and a threshold value may dictate automation of drug delivery, enablement of manual drug delivery, alerts being communicated, and/or various other types of responses through PRU (70) and/or BMU (40). In some instances, it may be useful to trigger such events based on trends in data rather than merely triggering such events based on where a parameter value lies in relation to a threshold value at a given moment. For instance, a safety shell may trigger an alarm when a patient's heart rate decreases rapidly and dramatically. This alarm may be triggered before the patient's heart rate actually falls below a predefined level. As another merely illustrative example, a PRU (70) may automatically deliver a drug or increase delivery of a drug in response to a patient's heart rate increasing, without necessarily waiting for the heart rate to exceed a certain threshold. As yet another merely illustrative example, a PRU (70) may automatically decrease the delivery of a drug in response to detected arterial desaturation and/or stop a drug in response to detected apena. Either or both screens (42, 72) may also display trends in physiological data, such as by showing a line fit over measured data.

There are various ways in which event triggering trends could be defined and/or applied. For instance, one way may involve creating a linear best fit to the data over a time period; either user defined, static, or dynamic based on data resolution or sensitivity patterns. If a linear best fit had a sufficient correlation coefficient, then the presence of the trend could be confirmed. The slope of the trend could be compared to a threshold slope. If the slope exceeds a predetermined value, then the trend could be confirmed (either positive or negative). It should also be understood that a trend could be logarithmic, exponential, or otherwise non-linear (e.g., depending on the data, the parameter, and the trend being observed, etc.). For instance, a separate alarm may be triggered in response to an extremely rapid exponential drop in a patient's saturation; while a lower priority alarm may be triggered for a gradual drop in heart rate. Various other suitable ways in which data trends may be incorporated into a safety shell control algorithm will be apparent to those of ordinary skill in the art in view of the teachings herein.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A medical system, comprising:
   (a) a first sedation system, the sedation system comprising:
      (i) a monitoring unit, wherein the monitoring unit is operable to monitor at least one physiological parameter of a patient, and
      (ii) a drug delivery unit, wherein the drug delivery unit is in communication with the monitoring unit, wherein the drug delivery unit is operable to at least partially automate delivery of one or more drugs to the patient based on the at least one physiological parameter of the patient; and
   (b) a central station, wherein the central station is in communication with the first sedation system, wherein the central station is also in communication with a at least one additional sedation system simultaneously, wherein the central station is operable to store patient related data, wherein the central station is further operable to individually access the first sedation system and the at least one additional sedation system;
   wherein each sedation system is operated in accordance with a respective safety shell control algorithm, wherein the central station is operable to remotely change the safety shell control algorithm associated with each sedation system.

2. The medical system of claim 1, wherein the central station is configured to process data from the first sedation system and the at least one additional sedation system, wherein the central station is further operable to selectively and remotely control drug delivery through the drug delivery unit of the first sedation system.

3. The medical system of claim 1, wherein the central station is operable to remotely provide a voice instruction through the first sedation system.

4. The medical system of claim 1, wherein the central station is operable to display a video feed providing a view of the patient associated with the first sedation system.

5. The medical system of claim 1, wherein the central station is operable to remotely change a drug delivery rate associated with the drug delivery unit of the first sedation system.

6. The medical system of claim 1, wherein the first sedation system is operable to query the central station and receive data from the central station in response to a query.

7. The medical system of claim 6, wherein the central station is operable to transmit data relating to steps of a medical procedure, to the first sedation system, in response to the query.

8. The medical system of claim 1, further comprising an instrument in communication with the first sedation system, wherein the instrument is operable to perform one or both of surgery on the patient or therapy on the patient.

9. The medical system of claim 8, wherein the first sedation system is operable to transmit data to the instrument, wherein the data relates to a physiological parameter of the patient, as monitored by the monitoring unit.

10. The medical system of claim 8, wherein the first sedation system is operable to at least partially control operation of the instrument based at least in part on data relating to a physiological parameter of the patient, as monitored by the monitoring unit, wherein the first sedation system is operable to at least partially disable the instrument based at least in part on data relating to a physiological parameter of the patient, as monitored by the monitoring unit.

11. The medical system of claim 8, wherein the first sedation system is configured to receive data from the instrument, wherein the first sedation system is operable to regulate the delivery of drugs through the drug delivery unit, based at least in part on data from the instrument, wherein the monitoring unit is operable to monitor a plurality of patient physiological parameters, wherein the drug delivery unit is configured to select one or more particular patient physiological parameters to process, based at least in part on data from the instrument.

12. The medical system of claim 8, wherein the first sedation system is configured to receive data from the instrument, wherein the monitoring unit is operable to monitor a plurality of patient physiological parameters, wherein the monitoring unit is configured to select one or more particular patient physiological parameters to monitor, based at least in part on data from the instrument.

13. The medical system of claim 8, wherein the first sedation system is operable to provide power to the instrument.

14. The medical system of claim 8, wherein the first sedation system is operable to communicate wirelessly with the instrument.

15. The medical system of claim 8, further comprising an adapter, wherein the instrument is coupled with the first sedation system via the adapter, wherein the adapter comprises one or both of a software adapter or firmware adapter configured to provide communication between software or firmware of the first sedation system and software or firmware of the instrument.

16. The medical system of claim 8, wherein the first sedation system includes a display screen, wherein the display screen is operable to display data from the monitoring unit, data from the drug delivery unit, and data from the instrument.

17. The medical system of claim 1, further comprising an earpiece in wireless communication with the first sedation system, wherein the first sedation system is operable to wirelessly transmit audible alerts or messages through the earpiece, based at least in part on data from the monitoring unit.

18. The medical system of claim 1, wherein the safety shell control algorithm is configured to restrict the delivery of drugs to prevent overmedication.

19. A medical system, comprising:
(a) a first sedation system and at least one additional sedation system wherein each sedation system comprises:
  (i) a monitoring unit, wherein the monitoring unit is operable to monitor at least one physiological parameter of a patient, and
  (ii) a drug delivery unit, wherein the drug delivery unit is in communication with the monitoring unit, wherein the drug delivery unit is operable to at least partially automate delivery of one or more drugs to the patient based on the at least one physiological parameter of the patient; and
(b) a central station, wherein the central station is in communication with the first sedation system and the at least one additional sedation system simultaneously, wherein the central station is further operable to selectively and remotely control drug delivery through the drug delivery unit of each of the sedation systems:,
wherein each sedation system is operated in accordance with a safety shell control algorithm wherein the central station is operable to remotely change the safety shell control algorithm associated with each sedation system.

* * * * *